(12) United States Patent
Fukuda et al.

(10) Patent No.: US 8,357,782 B2
(45) Date of Patent: Jan. 22, 2013

(54) MONOCLONAL ANTIBODIES SPECIFIC FOR HUMAN INTERFERON-ALPHA SUBTYPE ALPHA 8

(75) Inventors: Shigeharu Fukuda, Okayama (JP); Chie Ushio, Okayama (JP); Harumi Ariyasu, Okayama (JP); Tohru Kayano, Okayama (JP); Toshio Ariyasu, Okayama (JP); Tsunetaka Ohta, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 44 days.

(21) Appl. No.: 12/933,768

(22) PCT Filed: Mar. 16, 2009

(86) PCT No.: PCT/JP2009/055039
§ 371 (c)(1),
(2), (4) Date: Sep. 21, 2010

(87) PCT Pub. No.: WO2009/116491
PCT Pub. Date: Sep. 24, 2009

(65) Prior Publication Data
US 2011/0091968 A1    Apr. 21, 2011

(30) Foreign Application Priority Data
Mar. 21, 2008 (JP) ................................ 2008-072729
Jun. 6, 2008 (JP) ................................ 2008-149916

(51) Int. Cl.
*C07K 16/24* (2006.01)
*A61K 39/395* (2006.01)
*C12N 5/12* (2006.01)
(52) U.S. Cl. ................. 530/388.23; 424/145.1; 435/335
(58) Field of Classification Search .................. None
See application file for complete search history.

(56) References Cited

U.S. PATENT DOCUMENTS
2007/0014724 A1    1/2007    Witte et al.

FOREIGN PATENT DOCUMENTS

| EP | 915099 A1 | 5/1999 |
|---|---|---|
| EP | 1842857 A1 | 10/2007 |
| JP | 6-11235 B2 | 2/1994 |
| JP | 9-509955 A | 10/1997 |
| JP | 2004-533217 A | 11/2004 |
| JP | 2007-063177 | 3/2007 |
| JP | 2007-252372 A | 10/2007 |
| WO | WO 2006051805 A1 | 5/2006 |

OTHER PUBLICATIONS

Paul, W.E. Fundamental Immunology, 3rd Edition, 1993, pp. 292-295.*

Kaser et al., A., "Interferon-alpha in Inflammation and Immunity" Cellular and Molecular Biology, CMB Associations, Noisy-Le-Grand, FR, vol. 47, No. 4, Jan. 1, 2001, pp. 609-617, XP008083159, ISSN:0145-5680.
Ladoyanni et al., E., "Psoriasis Exacerbated by Interferon-alpha in a Patient with Chronic Myeloid Leukemia", Journal of Drugs in Dermatology, Strategic Communication in Dermatology, New York, NY US, vol. 4, No. 2, Mar. 1, 2005, pp. 221-222, XP009144864, ISSN: 1545-9616.
Yanai, et al., "Analysis of the Antiviral Activities of Natural IFN-alpha Preparations and Their Subtype Compositions", Journal of Interferon & Cytokine Research, 2001, pp. 835-841, vol. 21, No. 10.
Overall, et al., "Functional Analysis of Interferon-alpha Subtypes Using Monoclonal Antibodies to Interferon-alpha4a-Subtype Reactivity, Neutralisation of Biological Activities and Epitope Analysis", Molecular Immunology, 1992, pp. 391-399, vol. 29, No. 3.
Fukuda, et al., "Simultaneous Production of Natural Human Tumor Necrosis Factor-alpha, -Beta and Interferon-alpha from BALL-1 Cells Stimulated by HVJ", Lymphokine, 1988, pp. 175-185, vol. 7, No. 2.
Sato, et al., "Hito Jin Saibo Gan Saibo ni Taisuru Interferon alpha subtype ni yoru Koshuyo Koka no. Chigai", The 94th Japanese Journal of Urology, 2006, p. 417 (MP-204), vol. 97, No. 2. (with english translation).
Vacova, et al., The Carboxyterminal Domains of Human IFN-alpha2 and IFN-alpha8 Are Antigenically Homologous, Journal of Interferon and Cytokine Research, 2000, pp. 455-461, vol. 20, No. 5.
Ushio, et al. "Establishment of Antihuman IFN-alpha8-Specific Monoclonal Antibodies and Their Application in the Enzyme-Linked Immunosorbent Assay (ELISA),"Journal of Interferon and Cyokine Research, 2008, pp. 359-366, vol. 28, No. 6.

* cited by examiner

*Primary Examiner* — Robert Landsman
*Assistant Examiner* — Bruce D Hissong
(74) *Attorney, Agent, or Firm* — Browdy and Neimark, PLLC

(57) ABSTRACT

The present invention has the first object to provide a monoclonal antibody specific to interferon α subtype α8 (IFNα8) and its mutant proteins, the second object to provide a hybridoma capable of producing the monoclonal antibody, the third object to provide a method for detecting the IFNα8 and its mutant proteins by the monoclonal antibody, the fourth object to provide a method for purifying the IFNα8 and its mutant proteins by the monoclonal antibody, and the fifth object to provide a therapeutic agent for treating diseases whose onsets or exacerbation are related with IFNα8. The present invention solves the above objects by providing a monoclonal antibody specific to IFNα8 and its mutant proteins, a hybridoma capable of producing the monoclonal antibody, a method for detecting the IFNα8 and its mutant proteins by immunoreaction using the monoclonal antibody, a method for purifying the IFNα8 and its mutant proteins using the monoclonal antibody, and a therapeutic agent for treating diseases whose onsets or exacerbation are related with IFNα8, which contains the monoclonal antibody as an effective ingredient.

4 Claims, 1 Drawing Sheet

SEQUENCE LISTING

<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: T3 primer

<400> SEQUENCE: 1
aattaaccct cactaaaggg                                                    20

<210> SEQ ID NO 2
<211> LENGTH: 22
<212> TYPE: DNA
<213> ORGANISM: Artificial Sequence
<220> FEATURE:
<223> OTHER INFORMATION: T7 primer

<400> SEQUENCE: 2
gtaatacgac tcactatagg gc                                                 22

<210> SEQ ID NO 3
<211> LENGTH: 400
<212> TYPE: DNA
<213> ORGANISM: murine

<400> SEQUENCE: 3

```
c ctg gtg aca ttc cca agc tgt gtc cta tcc cag gtg cag ctg aag cag      49
  Leu Val Thr Phe Pro Ser Cys Val Leu Ser Gln Val Gln Leu Lys Gln
   1               5                  10                  15 tca gga cct ggc cta gtg cag ccc tca cag agc ctg tcc atc acc tgc         97
Ser Gly Pro Gly Leu Val Gln Pro Ser Gln Ser Leu Ser Ile Thr Cys
             20                  25                  30 aca gtc tct ggt ttc tca tta act agc tat ggt gta cac tgg att cgc        145
Thr Val Ser Gly Phe Ser Leu Thr Ser Tyr Gly Val His Trp Ile Arg
         35                  40                  45 cag tct cca gga aag ggt ctg gag tgg ctg gga gtg ata tgg agt ggt        193
Gln Ser Pro Gly Lys Gly Leu Glu Trp Leu Gly Val Ile Trp Ser Gly
     50                  55                  60 gga aac aca gac tat aat gca gct ttc att tcc aga ctg agc atc acc        241
Gly Asn Thr Asp Tyr Asn Ala Ala Phe Ile Ser Arg Leu Ser Ile Thr
 65                  70                  75                  80 aag gac aat tcc aag agc caa ttt ttc ttt aaa atg aac agt ctg caa        289
Lys Asp Asn Ser Lys Ser Gln Phe Phe Phe Lys Met Asn Ser Leu Gln
                 85                  90                  95 gct aaa gac aca gcc ata tat tac tgt gcc aga ggt aga ggg aat tac        337
Ala Lys Asp Thr Ala Ile Tyr Tyr Cys Ala Arg Gly Arg Gly Asn Tyr
             100                 105                 110 gtt ccc ttt act tat tgg ggc caa ggg act ctg gtc act gtc tct gca        385
Val Pro Phe Thr Tyr Trp Gly Gln Gly Thr Leu Val Thr Val Ser Ala
         115                 120                 125 gcc aaa acg aca ccc                                                    400
Ala Lys Thr Thr Pro
     130
```

<210> SEQ ID NO 4
<211> LENGTH: 400
<212> TYPE: DNA
<213> ORGANISM: murine

<400> SEQUENCE: 4

```
c ctg gtg aca ttc cca agc tgt gtc cta tcc cag gtg cag ctg aag cag      49
  Leu Val Thr Phe Pro Ser Cys Val Leu Ser Gln Val Gln Leu Lys Gln
   1               5                  10                  15 tca gga cct ggc cta gtg cag ccc tca cag agc ctg tcc atc acc tgc        97
Ser Gly Pro Gly Leu Val Gln Pro Ser Gln Ser Leu Ser Ile Thr Cys
             20                  25                  30 aca gtc tct ggt atc tca tta act agc tat ggt gta cac tgg att cgc       145
Thr Val Ser Gly Ile Ser Leu Thr Ser Tyr Gly Val His Trp Ile Arg
         35                  40                  45 cag tct cca gga aag ggt ctg gag tgg ctg gga gtg ata tgg agt ggt       193
Gln Ser Pro Gly Lys Gly Leu Glu Trp Leu Gly Val Ile Trp Ser Gly
     50                  55                  60 gga aac aca gac tat aat gca gct ttc att tcc aga ctg agc acc acc       241
Gly Asn Thr Asp Tyr Asn Ala Ala Phe Ile Ser Arg Leu Ser Thr Thr
 65                  70                  75                  80 aag gac aat tcc aag agc caa ttt ttc ttt aaa atg aac agt ctg caa       289
Lys Asp Asn Ser Lys Ser Gln Phe Phe Phe Lys Met Asn Ser Leu Gln
                 85                  90                  95 gct aaa gac aca gcc ata tat tac tgt gcc aga ggt aga ggg aat tac       337
Ala Lys Asp Thr Ala Ile Tyr Tyr Cys Ala Arg Gly Arg Gly Asn Tyr
            100                 105                 110 gtt ccc ttt act tat tgg ggc caa ggg act ctg gtc act gtc tct gca       385
Val Pro Phe Thr Tyr Trp Gly Gln Gly Thr Leu Val Thr Val Ser Ala
        115                 120                 125 gcc aaa acg aca ccc                                                    400
Ala Lys Thr Thr Pro
    130
```

<210> SEQ ID NO 5
<211> LENGTH: 388
<212> TYPE: DNA
<213> ORGANISM: murine

<400> SEQUENCE: 5

```
c ctg cta atc agt gcc tca gtc ata atg tcc aga gga caa att gtt ctc      49
  Leu Leu Ile Ser Ala Ser Val Ile Met Ser Arg Gly Gln Ile Val Leu
   1               5                  10                  15 acc cag tct cca aca atc atg tct gca tct cta ggg gaa cgg gtc acc        97
Thr Gln Ser Pro Thr Ile Met Ser Ala Ser Leu Gly Glu Arg Val Thr
             20                  25                  30 atg acc tgc act gcc agc tca agt gta agt tcc act tac ttg cac tgg       145
Met Thr Cys Thr Ala Ser Ser Ser Val Ser Ser Thr Tyr Leu His Trp
         35                  40                  45 tac cag cag aag cca gga tcc tcc ccc aaa ctc ttg att tat agc aca       193
Tyr Gln Gln Lys Pro Gly Ser Ser Pro Lys Leu Leu Ile Tyr Ser Thr
     50                  55                  60 tcc aac ctg gct tct gga gtc cca gct cgc ttc agt ggc agt ggg tct       241
Ser Asn Leu Ala Ser Gly Val Pro Ala Arg Phe Ser Gly Ser Gly Ser
 65                  70                  75                  80 ggg acc tct tac tct ctc aca atc agc aac atg gag gct gaa gat gct       289
Gly Thr Ser Tyr Ser Leu Thr Ile Ser Asn Met Glu Ala Glu Asp Ala
                 85                  90                  95 gcc act tat tac tgc cac cag tat cat cgt tcc cca ccc atg acg ttc       337
Ala Thr Tyr Tyr Cys His Gln Tyr His Arg Ser Pro Pro Met Thr Phe
            100                 105                 110
```

```
            ggt gga ggc acc aag ctg gaa atc aaa cgg gct gat gct gca cca act    385
            Gly Gly Gly Thr Lys Leu Glu Ile Lys Arg Ala Asp Ala Ala Pro Thr
                    115                 120                 125 gta                                                                388
            Val
```

<210> SEQ ID NO 6
<211> LENGTH: 133
<212> TYPE: PRT
<213> ORGANISM: murine

<400> SEQUENCE: 6

```
Leu Val Thr Phe Pro Ser Cys Val Leu Ser Gln Val Gln Leu Lys Gln
  1               5                  10                  15

Ser Gly Pro Gly Leu Val Gln Pro Ser Gln Ser Leu Ser Ile Thr Cys
             20                  25                  30

Thr Val Ser Gly Phe Ser Leu Thr Ser Tyr Gly Val His Trp Ile Arg
         35                  40                  45

Gln Ser Pro Gly Lys Gly Leu Glu Trp Leu Gly Val Ile Trp Ser Gly
     50                  55                  60

Gly Asn Thr Asp Tyr Asn Ala Ala Phe Ile Ser Arg Leu Ser Ile Thr
 65                  70                  75                  80

Lys Asp Asn Ser Lys Ser Gln Phe Phe Lys Met Asn Ser Leu Gln
                 85                  90                  95

Ala Lys Asp Thr Ala Ile Tyr Tyr Cys Ala Arg Gly Arg Gly Asn Tyr
            100                 105                 110

Val Pro Phe Thr Tyr Trp Gly Gln Gly Thr Leu Val Thr Val Ser Ala
            115                 120                 125

Ala Lys Thr Thr Pro
            130
```

<210> SEQ ID NO 7
<211> LENGTH: 133
<212> TYPE: PRT
<213> ORGANISM: murine

<400> SEQUENCE: 7

```
Leu Val Thr Phe Pro Ser Cys Val Leu Ser Gln Val Gln Leu Lys Gln
  1               5                  10                  15

Ser Gly Pro Gly Leu Val Gln Pro Ser Gln Ser Leu Ser Ile Thr Cys
             20                  25                  30

Thr Val Ser Gly Ile Ser Leu Thr Ser Tyr Gly Val His Trp Ile Arg
         35                  40                  45

Gln Ser Pro Gly Lys Gly Leu Glu Trp Leu Gly Val Ile Trp Ser Gly
     50                  55                  60

Gly Asn Thr Asp Tyr Asn Ala Ala Phe Ile Ser Arg Leu Ser Thr Thr
 65                  70                  75                  80

Lys Asp Asn Ser Lys Ser Gln Phe Phe Lys Met Asn Ser Leu Gln
                 85                  90                  95

Ala Lys Asp Thr Ala Ile Tyr Tyr Cys Ala Arg Gly Arg Gly Asn Tyr
            100                 105                 110

Val Pro Phe Thr Tyr Trp Gly Gln Gly Thr Leu Val Thr Val Ser Ala
            115                 120                 125

Ala Lys Thr Thr Pro
            130
```

```
<210> SEQ ID NO 8
<211> LENGTH: 129
<212> TYPE: PRT
<213> ORGANISM: murine

<400> SEQUENCE: 8

Leu Leu Ile Ser Ala Ser Val Ile Met Ser Arg Gly Gln Ile Val Leu
 1               5                  10                  15

Thr Gln Ser Pro Thr Ile Met Ser Ala Ser Leu Gly Glu Arg Val Thr
            20                  25                  30

Met Thr Cys Thr Ala Ser Ser Val Ser Ser Thr Tyr Leu His Trp
        35                  40                  45

Tyr Gln Gln Lys Pro Gly Ser Ser Pro Lys Leu Leu Ile Tyr Ser Thr
    50                  55                  60

Ser Asn Leu Ala Ser Gly Val Pro Ala Arg Phe Ser Gly Ser Gly Ser
65                  70                  75                  80

Gly Thr Ser Tyr Ser Leu Thr Ile Ser Asn Met Glu Ala Glu Asp Ala
                85                  90                  95

Ala Thr Tyr Tyr Cys His Gln Tyr His Arg Ser Pro Pro Met Thr Phe
            100                 105                 110

Gly Gly Gly Thr Lys Leu Glu Ile Lys Arg Ala Asp Ala Ala Pro Thr
        115                 120                 125

Val

<210> SEQ ID NO 9
<211> LENGTH: 128
<212> TYPE: PRT
<213> ORGANISM: murine

<400> SEQUENCE: 9

Leu Val Thr Phe Pro Ser Cys Val Leu Ser Gln Val Gln Leu Lys Gln
 1               5                  10                  15

Ser Gly Pro Gly Leu Val Gln Pro Ser Gln Ser Leu Ser Ile Thr Cys
            20                  25                  30

Thr Val Ser Gly Phe Ser Leu Thr Ser Tyr Gly Val His Trp Ile Arg
        35                  40                  45

Gln Ser Pro Gly Lys Gly Leu Glu Trp Leu Gly Val Ile Trp Ser Gly
    50                  55                  60

Gly Asn Thr Asp Tyr Asn Ala Ala Phe Ile Ser Arg Leu Ser Ile Thr
65                  70                  75                  80

Lys Asp Asn Ser Lys Ser Gln Phe Phe Phe Lys Met Asn Ser Leu Gln
                85                  90                  95

Ala Lys Asp Thr Ala Ile Tyr Tyr Cys Ala Arg Gly Arg Gly Asn Tyr
            100                 105                 110

Val Pro Phe Thr Tyr Trp Gly Gln Gly Thr Leu Val Thr Val Ser Ala
        115                 120                 125

<210> SEQ ID NO 10
<211> LENGTH: 128
<212> TYPE: PRT
<213> ORGANISM: murine

<400> SEQUENCE: 10

Leu Val Thr Phe Pro Ser Cys Val Leu Ser Gln Val Gln Leu Lys Gln
 1               5                  10                  15

Ser Gly Pro Gly Leu Val Gln Pro Ser Gln Ser Leu Ser Ile Thr Cys
            20                  25                  30
```

```
Thr Val Ser Gly Ile Ser Leu Thr Ser Tyr Gly Val His Trp Ile Arg
        35                  40                  45

Gln Ser Pro Gly Lys Gly Leu Glu Trp Leu Gly Val Ile Trp Ser Gly
    50                  55                  60

Gly Asn Thr Asp Tyr Asn Ala Ala Phe Ile Ser Arg Leu Ser Thr Thr
65                  70                  75                  80

Lys Asp Asn Ser Lys Ser Gln Phe Phe Lys Met Asn Ser Leu Gln
                85                  90                  95

Ala Lys Asp Thr Ala Ile Tyr Tyr Cys Ala Arg Gly Arg Gly Asn Tyr
                100                 105                 110

Val Pro Phe Thr Tyr Trp Gly Gln Gly Thr Leu Val Thr Val Ser Ala
            115                 120                 125

<210> SEQ ID NO 11
<211> LENGTH: 121
<212> TYPE: PRT
<213> ORGANISM: murine

<400> SEQUENCE: 11

Leu Leu Ile Ser Ala Ser Val Ile Met Ser Arg Gly Gln Ile Val Leu
1               5                   10                  15

Thr Gln Ser Pro Thr Ile Met Ser Ala Ser Leu Gly Glu Arg Val Thr
                20                  25                  30

Met Thr Cys Thr Ala Ser Ser Ser Val Ser Ser Thr Tyr Leu His Trp
        35                  40                  45

Tyr Gln Gln Lys Pro Gly Ser Ser Pro Lys Leu Leu Ile Tyr Ser Thr
    50                  55                  60

Ser Asn Leu Ala Ser Gly Val Pro Ala Arg Phe Ser Gly Ser Gly Ser
65                  70                  75                  80

Gly Thr Ser Tyr Ser Leu Thr Ile Ser Asn Met Glu Ala Glu Asp Ala
                85                  90                  95

Ala Thr Tyr Tyr Cys His Gln Tyr His Arg Ser Pro Pro Met Thr Phe
                100                 105                 110

Gly Gly Gly Thr Lys Leu Glu Ile Lys
            115                 120

<210> SEQ ID NO 12
<211> LENGTH: 388
<212> TYPE: DNA
<213> ORGANISM: rat

<400> SEQUENCE: 12 t gtc ctt tta ata aaa ggt gtt cag tgt gag gtg cag ctg gtg gag tct    49
  Val Leu Leu Ile Lys Gly Val Gln Cys Glu Val Gln Leu Val Glu Ser
    1               5                   10                  15 ggg gga ggc tta gtg cag ccc gga agg tcc ctg aaa ctc tcc tgt gca    97
Gly Gly Gly Leu Val Gln Pro Gly Arg Ser Leu Lys Leu Ser Cys Ala
                20                  25                  30 gcc tca gga ttc act ttc agt aaa tat ggc atg gcc tgg gtc cgc cag    145
Ala Ser Gly Phe Thr Phe Ser Lys Tyr Gly Met Ala Trp Val Arg Gln
        35                  40                  45 gct cca acg aag ggt ctg gag tgg gtc gca tcc att agt act ggt ggt    193
Ala Pro Thr Lys Gly Leu Glu Trp Val Ala Ser Ile Ser Thr Gly Gly
    50                  55                  60 tac aac act tac tat cga gac tcc gtg aag ggc cga ttc act att tcc    241
Tyr Asn Thr Tyr Tyr Arg Asp Ser Val Lys Gly Arg Phe Thr Ile Ser
65                  70                  75                  80
```

```
aga gat aat gca aaa aac acc caa tac ctg caa atg gac agt ctg agg      289
Arg Asp Asn Ala Lys Asn Thr Gln Tyr Leu Gln Met Asp Ser Leu Arg
             85                  90                  95 tct gag gac acg gcc act tat tac tgt aca aga ccc ccc gcg ttt gat      337
Ser Glu Asp Thr Ala Thr Tyr Tyr Cys Thr Arg Pro Pro Ala Phe Asp
            100                 105                 110 cac tgg ggc caa gga atc atg gtc aca gtc tcc tca gct gaa aca aca      385
His Trp Gly Gln Gly Ile Met Val Thr Val Ser Ser Ala Glu Thr Thr
        115                 120                 125 gcc                                                                  388
Ala

<210> SEQ ID NO 13
<211> LENGTH: 388
<212> TYPE: DNA
<213> ORGANISM: rat

<400> SEQUENCE: 13 t gtc ctt tta ata aaa ggt gtt cag tgt gag gtg cag ctg gtg gag tct   49
    Val Leu Leu Ile Lys Gly Val Gln Cys Glu Val Gln Leu Val Glu Ser
      1               5                  10                  15 ggg gga gac tta gtg cag ccc gga agg tcc ctg aaa ctc tcc tgt gca       97
Gly Gly Asp Leu Val Gln Pro Gly Arg Ser Leu Lys Leu Ser Cys Ala
             20                  25                  30 gcc tca gga ttc act ttc agt aaa tat ggc atg gcc tgg gtc cgc cag      145
Ala Ser Gly Phe Thr Phe Ser Lys Tyr Gly Met Ala Trp Val Arg Gln
         35                  40                  45 gct cca acg aag ggt ctg gag tgg gtc gca tcc att agt act ggt ggt      193
Ala Pro Thr Lys Gly Leu Glu Trp Val Ala Ser Ile Ser Thr Gly Gly
     50                  55                  60 tac aac act tac tat cga gac tcc gtg aag ggc cga ttc act att tcc      241
Tyr Asn Thr Tyr Tyr Arg Asp Ser Val Lys Gly Arg Phe Thr Ile Ser
 65                  70                  75                  80 aga gat aat gca aaa aac acc caa tac ctg caa atg gac agt ctg agg      289
Arg Asp Asn Ala Lys Asn Thr Gln Tyr Leu Gln Met Asp Ser Leu Arg
             85                  90                  95 tct gag gac acg gcc act tat tac tgt aca aga ccc ccc gcg ttt gat      337
Ser Glu Asp Thr Ala Thr Tyr Tyr Cys Thr Arg Pro Pro Ala Phe Asp
            100                 105                 110 cac tgg ggc caa gga atc atg gtc aca gtc tcc tca gct gaa aca aca      385
His Trp Gly Gln Gly Ile Met Val Thr Val Ser Ser Ala Glu Thr Thr
        115                 120                 125 gcc                                                                  388
Ala

<210> SEQ ID NO 14
<211> LENGTH: 363
<212> TYPE: DNA
<213> ORGANISM: rat

<400> SEQUENCE: 14 ctc cca gcc atg aga tgt gac atc aag atg acc cag tct cct tca ttc       48
Leu Pro Ala Met Arg Cys Asp Ile Lys Met Thr Gln Ser Pro Ser Phe
  1               5                  10                  15 ctg tct gca tct gtg gga gac aga gtc act atc aac tgc aaa gca agt       96
Leu Ser Ala Ser Val Gly Asp Arg Val Thr Ile Asn Cys Lys Ala Ser
             20                  25                  30 cag aat att gac aag tac tta aac tgg tat cag caa aag ctt gga aaa      144
Gln Asn Ile Asp Lys Tyr Leu Asn Trp Tyr Gln Gln Lys Leu Gly Lys
         35                  40                  45
```

```
gct ccc aga ctc ctg atg tat aat aca aac aat ttg caa acg ggc atc      192
Ala Pro Arg Leu Leu Met Tyr Asn Thr Asn Asn Leu Gln Thr Gly Ile
50                  55                  60 cca tca agg ttc agt ggc agt gga tct act act gat ttc aca ctc acc      240
Pro Ser Arg Phe Ser Gly Ser Gly Ser Thr Thr Asp Phe Thr Leu Thr
65                  70                  75                  80 atc agc agc ctg cag cct gaa gat gtt gcc aca tat ttc tgc tcg cac      288
Ile Ser Ser Leu Gln Pro Glu Asp Val Ala Thr Tyr Phe Cys Ser His
                85                  90                  95 cat agt gtt agg ccg tat acg ttt gga gct ggg acc aag ctg gaa ctg      336
His Ser Val Arg Pro Tyr Thr Phe Gly Ala Gly Thr Lys Leu Glu Leu
            100                 105                 110 aaa cgg gct gat gct gca cca act gta                                  363
Lys Arg Ala Asp Ala Ala Pro Thr Val
115                 120
```

<210> SEQ ID NO 15
<211> LENGTH: 129
<212> TYPE: PRT
<213> ORGANISM: rat

<400> SEQUENCE: 15

```
Val Leu Leu Ile Lys Gly Val Gln Cys Glu Val Gln Leu Val Glu Ser
1               5                   10                  15

Gly Gly Gly Leu Val Gln Pro Gly Arg Ser Leu Lys Leu Ser Cys Ala
            20                  25                  30

Ala Ser Gly Phe Thr Phe Ser Lys Tyr Gly Met Ala Trp Val Arg Gln
        35                  40                  45

Ala Pro Thr Lys Gly Leu Glu Trp Val Ala Ser Ile Ser Thr Gly Gly
    50                  55                  60

Tyr Asn Thr Tyr Tyr Arg Asp Ser Val Lys Gly Arg Phe Thr Ile Ser
65                  70                  75                  80

Arg Asp Asn Ala Lys Asn Thr Gln Tyr Leu Gln Met Asp Ser Leu Arg
                85                  90                  95

Ser Glu Asp Thr Ala Thr Tyr Tyr Cys Thr Arg Pro Pro Ala Phe Asp
            100                 105                 110

His Trp Gly Gln Gly Ile Met Val Thr Val Ser Ser Ala Glu Thr Thr
        115                 120                 125

Ala
```

<210> SEQ ID NO 16
<211> LENGTH: 129
<212> TYPE: PRT
<213> ORGANISM: rat

<400> SEQUENCE: 16

```
Val Leu Leu Ile Lys Gly Val Gln Cys Glu Val Gln Leu Val Glu Ser
1               5                   10                  15

Gly Gly Asp Leu Val Gln Pro Gly Arg Ser Leu Lys Leu Ser Cys Ala
            20                  25                  30

Ala Ser Gly Phe Thr Phe Ser Lys Tyr Gly Met Ala Trp Val Arg Gln
        35                  40                  45

Ala Pro Thr Lys Gly Leu Glu Trp Val Ala Ser Ile Ser Thr Gly Gly
    50                  55                  60

Tyr Asn Thr Tyr Tyr Arg Asp Ser Val Lys Gly Arg Phe Thr Ile Ser
65                  70                  75                  80

Arg Asp Asn Ala Lys Asn Thr Gln Tyr Leu Gln Met Asp Ser Leu Arg
                85                  90                  95
```

Ser Glu Asp Thr Ala Thr Tyr Tyr Cys Thr Arg Pro Pro Ala Phe Asp
            100                 105                 110

His Trp Gly Gln Gly Ile Met Val Thr Val Ser Ser Ala Glu Thr Thr
            115                 120                 125

Ala

<210> SEQ ID NO 17
<211> LENGTH: 121
<212> TYPE: PRT
<213> ORGANISM: rat

<400> SEQUENCE: 17

Leu Pro Ala Met Arg Cys Asp Ile Lys Met Thr Gln Ser Pro Ser Phe
1               5                   10                  15

Leu Ser Ala Ser Val Gly Asp Arg Val Thr Ile Asn Cys Lys Ala Ser
            20                  25                  30

Gln Asn Ile Asp Lys Tyr Leu Asn Trp Tyr Gln Gln Lys Leu Gly Lys
        35                  40                  45

Ala Pro Arg Leu Leu Met Tyr Asn Thr Asn Asn Leu Gln Thr Gly Ile
    50                  55                  60

Pro Ser Arg Phe Ser Gly Ser Gly Ser Thr Thr Asp Phe Thr Leu Thr
65                  70                  75                  80

Ile Ser Ser Leu Gln Pro Glu Asp Val Ala Thr Tyr Phe Cys Ser His
                85                  90                  95

His Ser Val Arg Pro Tyr Thr Phe Gly Ala Gly Thr Lys Leu Glu Leu
            100                 105                 110

Lys Arg Ala Asp Ala Ala Pro Thr Val
            115                 120

<210> SEQ ID NO 18
<211> LENGTH: 124
<212> TYPE: PRT
<213> ORGANISM: rat

<400> SEQUENCE: 18

Val Leu Leu Ile Lys Gly Val Gln Cys Glu Val Gln Leu Val Glu Ser
1               5                   10                  15

Gly Gly Gly Leu Val Gln Pro Gly Arg Ser Leu Lys Leu Ser Cys Ala
            20                  25                  30

Ala Ser Gly Phe Thr Phe Ser Lys Tyr Gly Met Ala Trp Val Arg Gln
        35                  40                  45

Ala Pro Thr Lys Gly Leu Glu Trp Val Ala Ser Ile Ser Thr Gly Gly
    50                  55                  60

Tyr Asn Thr Tyr Tyr Arg Asp Ser Val Lys Gly Arg Phe Thr Ile Ser
65                  70                  75                  80

Arg Asp Asn Ala Lys Asn Thr Gln Tyr Leu Gln Met Asp Ser Leu Arg
                85                  90                  95

Ser Glu Asp Thr Ala Thr Tyr Tyr Cys Thr Arg Pro Pro Ala Phe Asp
            100                 105                 110

His Trp Gly Gln Gly Ile Met Val Thr Val Ser Ser
            115                 120

<210> SEQ ID NO 19
<211> LENGTH: 124
<212> TYPE: PRT
<213> ORGANISM: rat

-continued

```
<400> SEQUENCE: 19

Val Leu Leu Ile Lys Gly Val Gln Cys Glu Val Gln Leu Val Glu Ser
1               5                   10                  15

Gly Gly Asp Leu Val Gln Pro Gly Arg Ser Leu Lys Leu Ser Cys Ala
            20                  25                  30

Ala Ser Gly Phe Thr Phe Ser Lys Tyr Gly Met Ala Trp Val Arg Gln
        35                  40                  45

Ala Pro Thr Lys Gly Leu Glu Trp Val Ala Ser Ile Ser Thr Gly Gly
    50                  55                  60

Tyr Asn Thr Tyr Tyr Arg Asp Ser Val Lys Gly Arg Phe Thr Ile Ser
65                  70                  75                  80

Arg Asp Asn Ala Lys Asn Thr Gln Tyr Leu Gln Met Asp Ser Leu Arg
                85                  90                  95

Ser Glu Asp Thr Ala Thr Tyr Tyr Cys Thr Arg Pro Pro Ala Phe Asp
            100                 105                 110

His Trp Gly Gln Gly Ile Met Val Thr Val Ser Ser
        115                 120

<210> SEQ ID NO 20
<211> LENGTH: 113
<212> TYPE: PRT
<213> ORGANISM: rat

<400> SEQUENCE: 20

Leu Pro Ala Met Arg Cys Asp Ile Lys Met Thr Gln Ser Pro Ser Phe
1               5                   10                  15

Leu Ser Ala Ser Val Gly Asp Arg Val Thr Ile Asn Cys Lys Ala Ser
            20                  25                  30

Gln Asn Ile Asp Lys Tyr Leu Asn Trp Tyr Gln Lys Leu Gly Lys
        35                  40                  45

Ala Pro Arg Leu Leu Met Tyr Asn Thr Asn Leu Gln Thr Gly Ile
    50                  55                  60

Pro Ser Arg Phe Ser Gly Ser Gly Ser Thr Thr Asp Phe Thr Leu Thr
65                  70                  75                  80

Ile Ser Ser Leu Gln Pro Glu Asp Val Ala Thr Tyr Phe Cys Ser His
                85                  90                  95

His Ser Val Arg Pro Tyr Thr Phe Gly Ala Gly Thr Lys Leu Glu Leu
            100                 105                 110

Lys

<210> SEQ ID NO 21
<211> LENGTH: 5
<212> TYPE: PRT
<213> ORGANISM: murine

<400> SEQUENCE: 21

Ser Tyr Gly Val His
1               5

<210> SEQ ID NO 22
<211> LENGTH: 16
<212> TYPE: PRT
<213> ORGANISM: murine

<400> SEQUENCE: 22

Val Ile Trp Ser Gly Gly Asn Thr Asp Tyr Asn Ala Ala Phe Ile Ser
1               5                   10                  15
```

-continued

<210> SEQ ID NO 23
<211> LENGTH: 10
<212> TYPE: PRT
<213> ORGANISM: murine

<400> SEQUENCE: 23

Gly Arg Gly Asn Tyr Val Pro Phe Thr Tyr
1               5                   10

<210> SEQ ID NO 24
<211> LENGTH: 12
<212> TYPE: PRT
<213> ORGANISM: murine

<400> SEQUENCE: 24

Thr Ala Ser Ser Ser Val Ser Ser Thr Tyr Leu His
1               5                   10

<210> SEQ ID NO 25
<211> LENGTH: 7
<212> TYPE: PRT
<213> ORGANISM: murine

<400> SEQUENCE: 25

Ser Thr Ser Asn Leu Ala Ser
1               5

<210> SEQ ID NO 26
<211> LENGTH: 10
<212> TYPE: PRT
<213> ORGANISM: murine

<400> SEQUENCE: 26

His Gln Tyr His Arg Ser Pro Pro Met Thr
1               5                   10

<210> SEQ ID NO 27
<211> LENGTH: 5
<212> TYPE: PRT
<213> ORGANISM: rat

<400> SEQUENCE: 27

Lys Tyr Gly Met Ala
1               5

<210> SEQ ID NO 28
<211> LENGTH: 17
<212> TYPE: PRT
<213> ORGANISM: rat

<400> SEQUENCE: 28

Ser Ile Ser Thr Gly Gly Tyr Asn Thr Tyr Tyr Arg Asp Ser Val Lys Gly
1               5                   10                  15

<210> SEQ ID NO 29
<211> LENGTH: 6
<212> TYPE: PRT
<213> ORGANISM: rat

<400> SEQUENCE: 29

Pro Pro Ala Phe Asp His
1               5

```
<210> SEQ ID NO 30
<211> LENGTH: 11
<212> TYPE: PRT
<213> ORGANISM: rat

<400> SEQUENCE: 30

Lys Ala Ser Gln Asn Ile Asp Lys Tyr Leu Asn
 1               5                  10

<210> SEQ ID NO 31
<211> LENGTH: 7
<212> TYPE: PRT
<213> ORGANISM: rat

<400> SEQUENCE: 31

Asn Thr Asn Asn Leu Gln Thr
 1               5

<210> SEQ ID NO 32
<211> LENGTH: 9
<212> TYPE: PRT
<213> ORGANISM: rat

<400> SEQUENCE: 32

Ser His His Ser Val Arg Pro Tyr Thr
 1               5
```

MONOCLONAL ANTIBODIES SPECIFIC FOR HUMAN INTERFERON-ALPHA SUBTYPE ALPHA 8

TECHNICAL FIELD

The present invention relates to a novel monoclonal antibody against human interferon-α (may be abbreviated as "IFN", hereinafter), more particularly, to a monoclonal antibody specific to human IFN-α subtype α8 ("human IFN-α subtype α8" will be abbreviated as "IFN-α8", hereinafter) and its mutant proteins.

BACKGROUND ART

IFN was first discovered as a virus-growth-inhibitory factor produced from virus-infected cells. There have been known that there are three different types of IFN, i.e., IFN-α/β, γ and λ with different receptors and there exist at least 13 different types of human IFN-α subtypes. Human IFN-α in the form of a recombinant preparation produced with *E. coli* or a natural preparation prepared by stimulating peripheral leukocytes or lymphoblastoid cells, as an established cell line, stimulated with Sendai Virus of Japan (HVJ). Such human IFN-α has been extensively, clinically used as therapeutics for malignant neoplasms such as renal cancer and type B/C hepatitis. IFN has been researched on its immunoregulatory action and its relation with autoimmune diseases such as allergic diseases and diabetics, as well as diseases induced by virus infections, and also it has been concerned on its in vivo dynamics. For assaying IFN activity, bioassay based on its anti-viral activity using culture cells has been used. Such bioassay well reflects the physiological activity of IFN, however, it is known that, for example, it requires considerably longer period of time for assaying and it is susceptible to factors that influence on the physiological functions of the cells used for assaying. When stimulated with viruses, etc., leukocytes and lymphoblastoids produce natural types of IFN including its plural types and subtypes (see, Yanai Y. et al., *Journal of Interferon & Cytokine Research*, Vol. 21, No. 10, pp. 835-841, 2001). Therefore, direct assay for activity of these subtypes and analysis of their functions were quite difficult.

Plurality of anti-human IFN-α monoclonal antibodies have been prepared to quantify and purify human IFN-α (see, for example, Japanese Patent Kokoku No. 11235/94, Japanese Patent Toku-Hyo 2004-533217, and Japanese Patent Kokai No. 2007-63177). A monoclonal antibody which specifically binds to human IFN-α subtype α4 ("human IFN-α subtype α4" will be abbreviated as "IFNα4", hereinafter) (see, for example, *Molecular Immunology*, Vol. 29, No. 3, pp. 391-399, 1992) has been prepared, and a kit for specific quantification of human IFN-α using a mouse monoclonal antibody has been commercialized (see, for example, "Kit for Assaying Human IFN-α", a product name of and commercialized by JIMORO Co., Ltd., Gunma, Japan), however, it could not specifically recognize IFN-α subtypes.

It is known that IFN-α8 exists in three types of molecules called IFNα8a, IFNα8b, and IFNα8c (see, for example, International Patent Publication No. WO 2006/051805). Since IFNα8 has a superior physiological activity to those of human IFNα subtypes α2a, α2b, etc., as conventional pharmaceutical ingredients, there has been proposed therapeutic medicaments for susceptive diseases, containing IFNα8 or mutant proteins thereof (see, for example, International Patent Publication No. WO 2006/051805 and Japanese Patent Toku-Hyo-Hei 9-509955). Since some of these human IFNα subtypes are pointed out that they possibly function as a co-agonist (an enhancer) for other subtypes (Japanese Patent Toku-Hyo-Hei 9-509955) and there exist IFNα8 mutant proteins with different specific activity (International Patent Publication No. WO 2006/051805), an assay system like bioassay, which specifically, accurately, and highly-sensitively quantifies proteins without being affected by other physiological factors, is required in case of researching physiological functions of human IFNα subtypes and mutant proteins thereof and studying through comparison of their physiological activity and blood dynamics in exploring medical preparations. Although monoclonal antibodies recognize specific epitopes but have different specificity and affinity, any monoclonal antibody suitable for constructing an assay system specific to IFNα8 and having high-sensitivity must be explored. To apply IFNα8 or its mutant proteins for pharmaceutical use, the above-identified IFNα8 and its mutant proteins should be purified specifically and massively, there needed is a monoclonal antibody suitable for preparing an antibody column, which has lesser non-specific adsorption on IFNs other than IFNα8 and its mutant proteins, and which facilitates the elution of IFNα8 and its mutant proteins from a column prepared with the monoclonal antibody.

DISCLOSURE OF INVENTION

Object of the Invention

The present invention has a first object to provide a monoclonal antibody specific to IFNα8 and its mutant proteins.

The present invention has a second object to provide a hybridoma capably of producing the monoclonal antibody.

The present invention has a third object to provide a method for detecting IFNα8 and its mutant proteins by using the monoclonal antibody.

The present invention has a fourth object to provide a method for purifying IFNα8 and its mutant proteins by using the monoclonal antibody.

The present invention has a fifth object to provide a therapeutic agent, which contains the monoclonal antibody as an effective ingredient, for viral diseases, autoimmune diseases, diabetics, psoriasis, rheumatoid arthritis, multiple sclerosis, Paget disease, hypoplastic anemia, nephritis, systemic lupus erythematosus, and/or immunodeficiency syndrome including after immunodeficiency syndrome.

Means to Attain the Object

To attains the above objects, the present inventors diligently studied a novel monoclonal antibody which specifically recognizes IFNα8 and its mutant proteins, and accomplished this invention.

The present invention has an embodiment as a gist, which provides a novel monoclonal antibody that specifically recognizes IFNα8 and its mutant proteins.

The other embodiment of the present invention is to provide a method for specifically detecting IFNα8 and its mutant proteins.

The another embodiment of the present invention is to provide a method for specifically purifying IFNα8 and its mutant proteins from a specimen containing the same along with impurities.

The another embodiment of the present invention is to provide a therapeutic agent for diseases such as allergic diseases, immunodeficiencies, and autoimmune diseases.

EFFECT OF THE INVENTION

The monoclonal antibody of the present invention specifically binds to IFNα8 and its mutant proteins but substantially does not bind to IFNs and their subtypes other than IFNα8 and its mutant proteins. Therefore, the monoclonal antibody of the present invention exhibits immunological reaction with only IFNα8 and its mutant proteins in test samples, and has a merit that it advantageously detects IFNα8 and its mutant proteins specifically, qualitatively, or quantitatively. The monoclonal antibody has a merit that it collects IFNα8 and its mutant proteins at a higher purity and efficiency from mixtures containing them along with impurities.

BEST MODE FOR CARRYING OUT THE INVENTION

Figure 1:
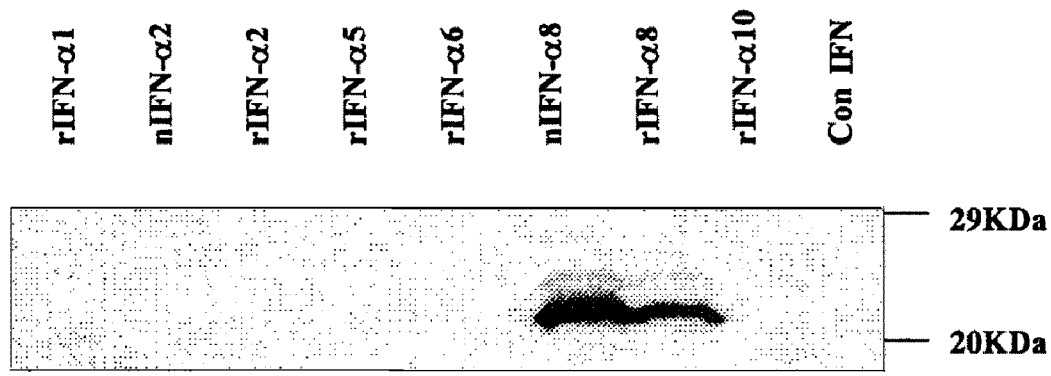
FIG. 1 is a figure for explaining an example of Western blotting of IFNs when IFNs were electrophoresed on SDS-polyacrylamide gel electrophoresis after charged on the gel in their respective amounts of 10 ng/lane, followed by transferring the IFNs contained in the gel to a nitrocellulose membrane and allowing the IFNs to react with the monoclonal antibody (α8#139mAb) of the present invention.

The term "IFNα8" as referred to as in the present invention means a conventionally known polypeptide, which has the amino acid sequence of IFNα8 disclosed in, for example, International Patent Publication No. 2006/051805, and means three types of polypeptides with an amino acid sequence consisting of 165 or 166 amino acid residues, where the amino terminus (called "N-terminus", hereinafter) begins with cysteine residue. These polypeptides may be called IFNα8a, IFNα8b, and IFNα8c (see, for example, International Patent Publication No. 2006/051805), and they may be totally called IFNα8 throughout the specification. As the polypeptides, those in the form of a natural, recombinant, or chemically-synthesized one can be used independently of their origins and sources.

The term "mutant proteins of IFNα8" as referred to as in the present invention includes polypeptides, wherein one or two but not more than several amino acids as constituents of a polypeptide having the amino acid sequence of IFNα8 are replaced with other amino acid(s), which have an antigenic determinant site recognized by monoclonal antibodies produced by hybridoma Mab-IFNα8#139 (FERM BP-11081, abbreviated as "α8#139" hereinafter) and mAb-IFNα8Y36-2 (FERN BP-11082, abbreviated as "α8Y36-2" hereinafter), and include those with the amino acid sequence of IFNα8 to which one or two but not more than several amino acids are added to the N-terminus and/or the carboxy terminus (called "C-terminus", hereinafter) and those with the amino acid sequence of IFNα8 wherein one or two but not more than several amino acids at the N-terminus and/or C-terminus are defected. Specifically, the followings are exemplified; polypeptides wherein the 145$^{th}$ arginine residue from the N-terminus of the amino acid sequence of IFNα8 is replaced with leucine, isoleucine or valine residue; those wherein the 146$^{th}$ alanine residue from the N-terminus of the amino acid sequence of IFNα8 is replaced with asparagine or serine residue; those wherein the 149$^{th}$ methionine residue from the N-terminus of the amino acid sequence of IFNα8 is replaced with tyrosine residue; and mutant polypeptides of the proceeding polypeptides wherein either or both of the 31$^{th}$ and 134$^{th}$ lysine residues from the N-terminus of the amino acid sequence of IFNα8 are retained but all of the other remaining lysine residues are replaced with other amino acid residues.

The term "monoclonal antibody" as referred to as in the present invention includes any monoclonal antibodies specific to the above-mentioned IFNα8 and its mutant proteins independently of their sources/origins, classes, or isotopes.

The monoclonal antibody of the present invention can be obtained by using, as an antigen, any of the above-identified IFNα8, its mutant proteins, and antigenic fragments thereof. Specifically, for example, the monoclonal antibody of the present invention can be obtained by preparing a hybridoma using both an antibody-producing cell collected from a mammal, which has been previously immunized with any of the above-identified antigens, and an infinitely-proliferating mammalian cell; selecting a clone of hybridoma capable of producing the monoclonal antibody; and culturing the selected clone in vitro.

IFNα8 and its mutant proteins usable as such an antigen should not be restricted to those from specific origins or preparation and include IFNα8 induced by adding a virus such as HVJ to lymphoblastoid cells such as BALL-1 cells, and other IFNα8 and its mutant proteins prepared by recombinant DNA technology or chemical synthetic method. Specifically, for example, IFNα8 derived from BALL-1 cells can be prepared by the method disclosed by Yanai Y. et al in *Journal of Interferon & Cytokine Research*, Vol. 21, No. 10, pp. 835-841 (2001); or IFNα8 or its mutant proteins can be prepared by the method disclosed in International Patent Publication No. WO 2006/051805. Usually, they are used in a completely or partially purified form. Antigenic fragments of the above IFNα8 or its mutant proteins are obtained by chemically or enzymatically decomposing them, or the desired peptides are synthesized based on the amino acid sequences of IFNα8a, IFNα8b, or IFNα8c disclosed in, for example, International Patent Publication No. 2006/051805.

Immunization can be carried out according to conventional method; any of the above-identified IFNα8, its mutant proteins, or fragments thereof is administered alone or in combination with an appropriate adjuvant to mammals intravenously, intradermally, intrasubcutaneously, or intraperitoneally before breeding the mammals for a prescribed period of time. The mammals should not specifically be restricted independently of their kind, size, or male and female, as long as the desired antibody-producing cells can be obtained. Usually, rodents such as rats, mice, and hamsters are used, and the most suitable mammal is selected through consideration of its adaptability to the later described infinitely-proliferating mammalian cells. Depending on the kind and size, the administration dose of an antigen is usually about 5 to about 500 µg/head in total to be administered to a mammal in a divided manner at a frequency of two to five times and at an interval of about one to about two weeks. On three to five days after the final administration, spleen is removed from the mammal and dispersed into spleen cells as antibody-producing cells.

The antibody-producing cells thus obtained are fused with infinitely-proliferating mammalian cells to obtain fused cells containing a desired hybridoma. Examples of the infinitely-proliferating mammalian cells include, usually, cell lines derived from mucus or rat myelomas such as P3-NS1-Ag4-1 cell (ATCC TIB18), P3-X63-Ag8 cell (ATCC TIB9), SP2/O—Ag14 cell (ATCC CRL1581), and Y3Ag1.2.3 cell (ATCC CRL1631), as well as mutant strains thereof. Cell fusion can be effected by, for example, a method using an electric pulsation or a cell-fusion-accelerating agent such as polyethylene glycol and HVJ. An example of such is as follows: Cell fusion is conducted by suspending antibody-producing cells and infinitely-proliferating mammalian cells in a cell ratio of about 1:1 to about 1:10 in a cell-fusion medium containing a cell-fusion-accelerator, and incubating them under such cell-suspension condition at about 30_C to about 40_C for about one to about five minutes. Examples of such a cell-fusion medium include those used in general such as MEM medium, RPMI1640 medium, Iscove's Modified Dulbecco's Medium (IMDM), in which sera such as calf serum should preferably be avoided.

To select desired hybridomas, the fused cells obtained in the above are transferred to a selection medium such as HAT medium and incubated at about 30° C. to about 40° C. for about three days to about three weeks to die cells other than the hybridomas. The resulting hybridomas are cultured in conventional manner, and the antibodies secreted in each culture are tested for reactivity with IFNα8 and its mutant proteins. In practicing the test, conventional methods for detecting antibodies such as enzyme immunoassay, radio immunoassay, and bioassay, as variously disclosed in detail, for example, in "*Tan-Clone-Kotai-Jikken-Manual* (Experimental Manual for Monoclonal Antibody)", edited by Sakuji TOYAMA and Tamie ANDO, published by Kodansha Scientific, Ltd., Tokyo, Japan, pp. 105-152 (1991). Hybridomas which produce antibodies specific to IFNα8 and its mutant proteins are directly cloned by limiting dilution, etc., to obtain the monoclonal hybridoma according to the present invention.

The monoclonal antibody of the present invention can be obtained by culturing such hybridomas in vivo or in vitro. In culturing, conventional methods for culturing mammalian cells are used; a method for culturing cells in a culture medium in vitro yields the monoclonal antibody from the resulting culture, and a method for culturing cells in vivo after transplanting any of the hybridomas to a warm-blooded animal other than humans yields the monoclonal antibody from the animal's ascites and/or blood. The monoclonal anti-IFNα8 antibody produced from the later described hybridomas α8#139 (deposited Feb. 15, 2008, under the terms of the Budapest Treaty in the International Patent Organism Depositry (IPOD), National Institute of Advanced Industrial Science and Technology under the accession number of FERM BP-11081) and α8Y36-2 (deposited Feb. 15, 2008, under the terms of the Budapest Treaty in the International Patent Organism Depositry (IPOD), National Institute of Advanced Industrial Science and Technology under the accession number of FERM BP-11082), have a lesser non-specific reaction and detect even a slight amount of IFNα8 specifically and sensitively, when used for detecting IFNα8 and its mutant proteins. These hybridomas are characteristic of that they are high in productivity of monoclonal antibody and easily cultured in vivo and in vitro. Conventional methods used in the art for purifying antibodies in general can be employed to collect the monoclonal antibodies from the above cultures, ascites or blood. Respective examples of such methods include salting out, dialysis, filtration, concentration, centrifugation, separatory sedimentation, gel filtration chromatography, ion-exchange chromatography, affinity chromatography, high-performance liquid chromatography (HPLC), gel electrophoresis, and electrofocusing, which can be applied in an appropriate combination, if necessary. The resulting purified monoclonal antibodies are successively concentrated, dried, and prepared into those in the form of a liquid or solid, depending on use.

The monoclonal antibody of the present invention can be also obtained by, for example, synthesizing a gene by polymerase chain reaction (PCR) or a chemical synthesis in such a manner of linking either a DNA which encodes heavy- and light-chain variable regions containing the nucleotide sequence of SEQ ID NO: 3 or 4 and the nucleotide sequence of SEQ ID NO: 5, or a DNA which encodes heavy- and light-chain variable regions containing the nucleotide sequence of SEQ ID NO: 12 or 13 and the nucleotide sequence of SEQ ID NO: 14, with a well-known DNA encoding heavy- and light-chain constant regions (see, for example, Japanese Patent Kokai No. 2007-252372); preparing a transformant by conventional method in such a manner of introducing the DNA thus obtained into conventional expression vector (pcDNA3.1 commercialized by Invitrogen), etc., capable of expressing the introduced gene; allowing the DNA to express in Chinese hamster ovary cells (CHO cells), *E. coli*, or the like to produce the desired antibody; and purifying the antibody in the resulting culture by using "PROTEIN A COLUMN" or the like.

The resulting antibody produced by these methods can be directly used intact to meet the following object, or it can be advantageously used as fragments such as Fv, scFv, Fab, F(ab'), and Fab', which include an antigen recognition site of the antibody, as long as it has a binding activity to IFNα8 and its mutant proteins.

The monoclonal antibody of the present invention has extensive uses in the field that requires detection of IFNα8 and/or its mutant proteins. When labelled immunoassay such as radioimmunoassay, enzyme immunoassay, and fluoroimmunoassay are applied to the monoclonal antibody of the present invention, any of IFNα8 and/or its mutant proteins present in a test sample can be specifically, promptly, and accurately assayed qualitatively or quantitatively. In practicing these assays, the monoclonal antibody of the present invention can be used after being labelled with, for example, radioactive substances, enzymes, and/or fluorescent substances. Since the monoclonal antibody of the present invention specifically reacts with IFNα8 and its mutant proteins, an extremely small amount of IFNα8 or its mutant proteins in a test sample can be accurately detected by measuring the above immunoreaction with an index of any of the above labelled substances. Compared to bioassay, labelled immunoassay has characteristics of that it can assay a plenty of samples simultaneously, requires lesser time and labor for assaying, and has a relatively high accuracy. The detection method according to the present invention is quite useful in controlling the steps for producing IFNα8 and/or its mutant proteins and for controlling the product quality, as well as in clinical diagnosis of IFNα8-related diseases. Although the present invention does not describe in detail the techniques for labelling monoclonal antibody or radio-labelled assay because it does not in itself relate to such an invention, techniques thereof are described in detail in "*Enzyme Immunoassay*", edited by P. Tijssen, translated by Eiji ISHIKAWA, published by Tokyo-Kagaku-Dojin, pp. 196-348 (1989). The monoclonal antibody of the present invention is the one that specifically recognizes IFNα8 and its mutant proteins, and it specifically detects IFNα8 and its mutant proteins when used in the form of an immobilized antibody and/or labelled antibody for enzyme immunoassay. Among which, when the monoclonal antibody of the present invention is applied to detect IFNα8 and its mutant proteins by using it as an immobilized antibody and labelled antibody in enzyme immunoassay by sandwich method, it constructs an assay system with high sensitivity that detects these proteins in the range of 50 to 2,000 pg/ml without substantially detecting any human IFNα subtypes other than IFNα8. To this aim, particularly, the following can be exemplified as monoclonal antibodies suitable for enzyme immunoassay with high sensitivity by sandwich method: Monoclonal antibodies produced by the later described hybridomas, α8#139 (deposited Feb. 15, 2008, under the terms of the Budapest Treaty in the International Patent Organism Depository (IPOD), National Institute of Advanced Industrial Science and Technology under the accession number of FERM BP-11081) and a8Y36-2 (deposited Feb. 15, 2008, under the terms of the Budapest Treaty in the International Patent Organism Depository (IPOD), National Institute of Advanced Industrial Science and Technology under the accession number of FERM BP-11082). In the case of using the two types of monoclonal antibodies as an immobilized or labelled antibody, human IFNα subtypes other than IFNα8 are not detected even at a concentration of 2,000 pg/ml and any non-specific adsorption reaction is hardly detected, while IFNα8 and its mutant proteins are accurately detected at a relatively high sensitivity.

The monoclonal antibody of the present invention is quite useful in purifying IFNα8 and its mutant proteins by immunoaffinity chromatography. This purification method contains both a step of allowing the monoclonal antibody of the present invention to contact with a mixture, containing IFNα8 and its mutant proteins along with concomitants including contaminated proteins other than the above IFNα8 and its mutant proteins, to adsorb only the IFNα8 and its mutant proteins on the monoclonal antibody, and a step of desorbing the adsorbed IFNα8 and its mutant proteins from the antibody, where the both steps are usually carried out in an aqueous solvent system. The monoclonal antibody of the present invention is usually used in the form of being bound to a water-insoluble gel carrier, and the resulting water-insoluble gel carrier is packed in a cylindrical tube, etc., to form a column, to which is fed, for example, a supernatant containing IFNα produced by stimulating BALL-1 cells, a lymphoblastoid cell line, with HVJ; a culture of a transformant capable of producing IFNα8 or its mutant protein(s); or a partially purified specimen of thereof, resulting in adsorption of substantially only IFNα8 and its mutant proteins on the monoclonal antibody immobilized on the water-insoluble gel carrier. The proteins adsorbed on the monoclonal antibody are easily desorbed by changing the pH around the antibody; in the case of using a monoclonal antibody belonging to IgG class, the elution of the proteins is effected at an acid pH, usually, a pH of 2 to 3, while in the case of using a monoclonal antibody belonging to IgM class, the elution is effected at an alkaline pH, usually, a pH of 10 to 11. As a monoclonal antibody suitable for such purpose, for example, those produced by the above-identified α8#139 and α8Y36-2 can be exemplified.

The monoclonal antibody of the present invention can be expressed in CHO cells or E. coli to produce chimera, humanized, or human antibodies by using the above-mentioned recombinant technology, etc., and these antibodies are prepared into fragments such as Fv, scFv, Fab, F(ab'), Fab', diabodies, and minibodies, which have an antigen recognition site(s) of the above antibodies; and used as effective ingredients for therapeutic agents to treat diseases such as viral diseases, allergic diseases, atopic diseases, autoimmune diseases, diabetics, psoriasis, rheumatoid arthritis, multiple sclerosis, Paget disease, hypoplastic anemia, nephritis, systemic lupus erythematosus, and/or immunodeficiency syndrome including after immunodeficiency syndrome, whose onset and exacerbation are related with IFNα8. Specific examples of the monoclonal antibodies usable as effective ingredients for such therapeutic agents include those produced by the above hybridomas, α8#139 and α8Y36-2, particularly, the one produced by the hybridoma α8#139 capable of neutralizing IFNα8 activity is preferable. The antibody produced by the later described hybridoma α8#S56-1 can be also advantageously used because it can neutralize IFNα8 activity. In such cases, these monoclonal antibodies can be made alone into pharmaceutical preparations, however, they can usually, preferably be made into pharmaceutical preparations incorporated with one or more pharmaceutically acceptable additives and optionally other effective ingredients usable in the treatment for the above-identified diseases. These pharmaceutical preparations can be usually administered intradermally, subcutaneously, intramuscularly, intravenously, or intraperitoneally, and the dose thereof is appropriately selected from those which exert a possible therapeutic effect on patients with diseases to be treated. Usually, the monoclonal antibody of the present invention can be administered to humans at a dose of 0.001 to 2,000 mg/day/adult, preferably, 0.01 to 1,000 mg/day/adult, more preferably, 0.1 to 1,000 mg/day/adult in whole or in a divided manner for one to several times of administration.

Now explaining more in detail the monoclonal antibody of the present invention suitable for the above mentioned immunoassay, purification of IFNα8 and its mutant proteins, and therapeutic agents for treating diseases whose onsets or exacerbation are related with IFNα8, any monoclonal antibodies can be used as long as they attain the objects of the present invention independently of their origins and amino acid sequences, particularly, the antibodies produced by the hybridomas, α8#139 and α8Y36-2, are desirable. Referring to the amino acid sequences, preferable are antibodies containing at least one of the amino acid sequences represented by SEQ ID NOs: 21 to 23 in their heavy-chain variable regions and/or at least one of the amino acid sequences represented by SEQ ID NOs: 24 to 26 in their light-chain variable regions; or others containing at least one of the amino acid sequences represented by SEQ ID NOs: 27 to 29 in their heavy-chain variable regions and/or at least one of the amino acid sequences represented by SEQ ID NOs: 30 to 32 in their light-chain variable regions. More preferable are antibodies containing all of the amino acid sequences represented by SEQ ID NOs: 21 to 23 in their heavy-chain variable regions and all of the amino acid sequences represented by SEQ ID NOs: 24 to 26 in their light-chain variable regions; or others containing all of the amino acid sequences represented by SEQ ID NOs: 27 to 29 in their heavy-chain variable regions and all of the amino acid sequences represented by SEQ ID NOs: 30 to 32 in their light-chain variable regions. Further, more preferable are antibodies containing the amino acid sequence represented by SEQ ID NO: 9 or 10 in their heavy-chain variable regions and the amino acid sequence represented by SEQ ID NO: 11 in their light-chain variable regions; or others containing the amino acid sequence represented by SEQ ID NO: 18 or 19 in their heavy-chain variable regions and the amino acid sequence represented by SEQ ID NO: 20 in their light-chain variable regions. Particularly, antibodies containing the amino acid sequence represented by SEQ ID NO: 9 or 10 in their heavy-chain variable regions and the amino acid sequence represented by SEQ ID NO: 11 in their light-chain variable regions is desirable because they have a satisfactory neutralizing activity for IFNα8 and a relatively high correlation with such activity.

By using these antibodies intact or their recombinants prepared by using their partial amino acid sequences or modifying 1 to about 100 amino acids thereof with deletion, addition or replacement; chimera, humanized or human antibodies which specifically recognize human IFNα8 and its mutant proteins and have applicability to quantification/qualification and purification of IFNα8 and to treatments and clinical diagnoses of IFNα8-related diseases can be advantageously prepared by conventional methods (see, for example, Japanese Patent Kokai Nos. 2004-533217 and 2007-252372). Usually, the deletion, addition, and replacement of amino acids are desirably made within several numbers of amino acids, preferably, 1 to 5, more preferably, 1 to 3, most preferably, 1 or 2 amino acids. These deletion, addition, and replacement can be introduced into hypervariable regions/sites that define antibodies' specificity and usually they are desirably introduced into other regions/sites.

The present invention will be explained with reference to the following Examples but it should never be limited thereby. Both the recombinant (recombinant may be abbreviated as "r", hereinafter) human IFNα subtypes containing IFNα8, and mutant proteins of IFNα8 used in the following Examples were prepared by using *E. coli* at Hayashibara Biochemical Laboratories, Inc., Okayama, Japan (see, Yanai Y. et al., in *Journal of Interferon & Cytokine Research*, Vol. 21, No. 10, pp. 835-841 (2001) and International Patent Publication No. WO 2006/051805). A peptide having the amino acid sequence of IFNα8b was used as rIFNα8 (see, International Patent Publication No. WO 2006/051805). Natural (natural may be abbreviated as "n", hereinafter) human IFNα subtype α2b (abbreviated as "IFNα2", hereinafter), nIFNα8, mouse IFNα/β, and rat IFNα were used those prepared at Hayashibara Biochemical Laboratories, Inc., (see, Yanai Y. et al., in *Journal of Interferon & Cytokine Research*, Vol. 21, No. 10, pp. 835-841 (2001)). Human IFNβ (abbreviated as "IFNβ", hereinafter) and consensus IFN (may be abbreviated as "Con IFN", hereinafter) used were respectively purchased from Mochida Pharmaceutical Co., Ltd., Tokyo, Japan, and Astellas Pharma Inc., Tokyo, Japan. Human IFNγ (abbreviated as "IFNγ", hereinafter) and human tumor necrosis factor (human TNFα, abbreviated as "TNFα", hereinafter) were products of COSMO BIO Co., Ltd., Tokyo, Japan, and purchased there from for use. The IFNs and cytokines (proteinaceous ingredients added for stabilization or the like are not included to determine their specific activities in Table 5) used in the following Examples are all shown in the later described Table 5. Human IFNα subtypes α1, α5, α6 and α10 are respectively abbreviated as IFNα1, IFNα5, IFNα6 and IFNα10, hereinafter. In the following Examples, mutant Nos. 2 and 3 in Experiments 1-1 to 1-3 disclosed by Yanai Y. et al., in *Journal of Interferon & Cytokine Research*, Vol. 21, No. 10, pp. 835-841 (2001), which are respectively a mutant protein of IFNα8 (abbreviated as "IFNα8-MUT2", hereinafter) that means IFNα8b consisting of 166 amino acid residues wherein the 145$^{th}$ arginine residue from the N-terminal cysteine residue has been replaced with isoleucine, the 146$^{th}$ alanine residue has been replaced with serine residue, and the 149$^{th}$ methionine residue has been replaced with thyronine; and another mutant protein of IFNα8 (abbreviated as "IFNα8-MUT3", hereinafter) which means IFNα8b consisting of 166 amino acid residues wherein the 145$^{th}$ arginine residue from the N-terminal cysteine residue has been replaced with leucine, the 146$^{th}$ alanine residue has been replaced with serine residue, and the 149$^{th}$ methionine residue has been replaced with thyronine.

EXAMPLE 1

<Preparation of Hybridoma Capable of Producing Mouse Anti-IFNα8 Antibody>
<Antigen>
rIFNα8, derived from *E. coli* and having a protein concentration of 510 μg/ml and an activity of $1.27 \times 10^8$ IU/ml, which had been prepared by the method disclosed in International Patent Publication No. WO 2006/051805, was used as an antigen. The titer of IFN (international unit: IU) was assayed on a bioassay with an index of inhibitory action of cytopathic effect by Sindbis virus on FL cells. In the assay, it was used a house standard specimen, which had been prepared at Hayashibara Biochemical Laboratories, Inc., Okayama, Japan, and assayed with an international standard specimen, Ga23-901-532.
<Immunization Method>
An emulsion was prepared by mixing the above antigen (10 μg/head) and Freund's complete adjuvant commercialized by DIFCO Laboratories, Inc., and intraperitoneally administered to mice (BALB/c, 9-week-old, female mice, commercialized by Charles River Laboratories Japan Inc., for immunization. From the 2nd immunization, the antigen was intraperitoneally administered three times in total at an interval of two weeks to the mice except for replacing the Freund's complete adjuvant with Freund's incomplete adjuvant commercialized by DIFCO Laboratories, Inc.
<Cell Fusion>
On seven days after the last immunization, the mice were partially collected blood from their tail veins for confirming antibody titer. Subjects, which had been confirmed with an increased antibody titer, were intravenously administered with 10 μg of the antigen free of adjuvant (called "intravenous injection", hereinafter) as a final immunization on three days before the following cell fusion. On three days after the intravenous infusion, spleen from any of the mice was in conventional manner collected and dispersed to obtain spleen cells. The spleen cells and a parent strain, i.e., mouse SP2/O—Ag14 cells (ATCC CRL1581), were respectively suspended in RPMI1640 medium (pH 7.2) free of serum, which had been prewarmed to 37° C. at respective cell densities of $2.5 \times 10^5$ cells/ml and $5 \times 10^4$ cells/ml, and centrifuged to collect a sedimented part. To the sedimented part was dropped over one minute one milliliter of RPMI1640 (pH 7.2) free of serum but containing 50% (w/v) polyethylene glycol with an average molecular weight of 1,500 daltons, and further RPMI1640 medium (pH 7.2) free of serum was dropped to the resulting mixture until the total volume reached 50 ml, followed by centrifuging the mixture to collect a sedimented part. The sedimented part was suspended in HAT medium, distributed to 96-well microplates by 200 μl/well, and incubated at 37° C. for two weeks to select hybridomas. The above-identified cell fusion was repeated trice by the similar method as in the above and by using the spleen obtained from one of the mice in each cell fusion. The cell supernatant in each well with proliferated hybridomas (may be called "culture supernatant of hybridomas", hereinafter) was collected and subjected to the later described enzyme immunoassay as a direct method to select hybridomas capable of producing an antibody having reactivity with rIFNα8. The hybridomas were successively subjected to repeated limiting dilution in conventional manner to obtain clones of hybridomas capable of stably producing monoclonal antibodies with affinity to rIFNα8, i.e., α8#44, α8#59, α8#98, α8#139, and α8#145. Among which, α8#139 or mAb-IFNα8#139 was deposited Feb. 18, 2008, under the terms of the Budapest Treaty in the International Patent Organism Depository (IPOD), National Institute of Advanced Industrial Science and Technology, Chuo-6,1-chome 1-1, Tsukuba-Higashi, Ibaraki, Japan, on Feb. 15, 2008, under the accession number of FERM BP-11081). The monoclonal antibodies produced by the above hybridomas can be used as antibodies for use in immunoassay for qualitative or quantitative analysis of IFNα8 and its mutant proteins, as well as in purification of such proteins. The monoclonal antibodies produced by the above hybridomas can be also used intact or after prepared into chimera, humanized, or human antibodies through recombinant DNA technology, etc., as effective ingredients for therapeutic agents for IFNα8-related diseases whose onset or exacerbation are related with IFNα8.

<Screening for Hybridomas Capable of Producing Anti-IFNα8 Antibody by Direct Method>

A fresh preparation of the rIFNα8 used as an antigen was diluted to give a protein concentration of two micrograms per milliliter, added to a covalent NH module, commercialized by Nunc Roskilde, Denmark, in a volume of 50 µl/well (a protein content of rIFNµ8: 100 ng/50 µl/well), and allowed to adsorb on the module with bis(sulfosuccinimidyl) suberate to form a solid phase. The solution containing rIFNα8 added to each well was removed, and the solid phase was subjected to a blocking treatment with PBS containing one percent of BSA, followed by removing the solution. To each well was added any of the above culture supernatants of hybridomas, followed by shaking at ambient temperature for two hours. After removing the supernatant, each well was washed with PBS containing 0.05% tween, and admixed with a rabbit anti-mouse immunoglobulin labelled with peroxidase (abbreviated as "HRP", hereinafter), commercialized by DakoCytomation, Denmark. After removing the solution containing the labelled antibody, each well was washed with PBS containing 0.05% tween, subjected to coloration reaction by adding 0.1 M sodium phosphate citrate buffer (pH 5.0) containing 0.5 mg/ml of o-phenylenediamine (abbreviated as "o-PD", hereinafter) and 0.03% hydrogen peroxide, admixed with 100 µl/well of 2 N $H_2SO_4$ to suspend the reaction, and subjected to measurement for absorption (OD: $A_{490}/_{650}$ nm) on a multi-plate reader to select a hybridoma capable of producing antibody having reactivity with rIFNα8.

EXAMPLE 2

<Preparation of Hybridomas Capable of Producing Rat Anti-IFNα8 Antibody> rIFNα8 used in Example 1, as an antigen, was kneaded with Freund's complete adjuvant, and the mixture was intraperitoneally administered to BN rats, 10-week-old, for immunization, in an amount of 20 µg/head in terms of the protein content. Thereafter, the rats were administered twice with the same amount of the antigen as used in the above after being mixed with Freund's incomplete adjuvant at two weeks interval, and on one week after the final administration the same amount of the antigen free of adjuvant as used in the above was intravenously administered to the rats. On three days after the intravenous administration, spleen of any of the rats was extracted and dispersed to obtain spleen cells. The spleen cells and Y3Ag1.2.3 cells (ATCC CRL1631) derived from rat myeloma were respectively suspended in RPMI1640 medium (pH 7.2) free of serum, which had been prewarmed to 37° C., at respective cell densities of $2.5 \times 10^5$ cells/ml and $5 \times 10^4$ cells/ml, and centrifuged to collect a sedimented part. To the sedimented part was dropped over one minute one milliliter of RPMI1640 (pH 7.2) free of serum but containing 50% (w/v) polyethylene glycol with an average molecular weight of 1,500 daltons, and the mixture was incubated at 37° C. for one minute and further dropped with RPMI1640 medium (pH 7.2) free of serum until the total volume reached 50 ml, followed by centrifuging the resulting mixture to collect a sedimented part. The sedimented part was suspended in HAT medium, distributed to 96-well microplates by 200 µl/well, and incubated at 37° C. for two weeks to obtain hybridomas. The antibody secreted in the culture supernatant in each well was assayed on the later described enzyme immunoassay by sandwich method to select hybridomas capable of producing an antibody having reactivity with rIFNα8. Subsequently, the hybridomas were repeatedly subjected to limit dilution in conventional manner to obtain clones of hybridomas, i.e., α8#Y19-1 and α8Y36-2, capable of stably producing the monoclonal antibody of the present invention. Among which, the clone of hybridoma α8Y36-2 or mAb-IFNα8Y36-2 was deposited Feb. 15, 2008, under the terms of the Budapest Treaty in the International Patent Organism Depository (IPOD), National Institute of Advanced Industrial Science and Technology, Chuo-6, 1-chome 1-1, Tsukuba-Higashi, Ibaraki, Japan, on Feb. 15, 2008, under the accession number of FERM BP-11082). The monoclonal antibodies produced by these hybridomas can be used as antibodies for use in immunoassay for qualitative or quantitative analysis of IFNα8 and its mutant proteins, as well as in purification of such proteins. The monoclonal antibodies produced by these hybridomas can be also used intact or after prepared into chimera, humanized, or human antibodies through recombinant DNA technology, etc., as effective ingredients for therapeutic agents for diseases whose onsets or exacerbation are related with IFNα8.

"IMMUNOPLATE" commercialized by Nunc Roskilde, Denmark, was coated with a rabbit anti-rat immunoglobulin commercialized by DakoCytomation, Denmark, admixed with any of the culture supernatants of hybridomas, and shaken at ambient temperature for one to two hours. After removing the supernatant, the resultant was washed trice with PBS containing 0.05% tween, admixed with 5 ng/50 µl/well of rIFNα8, and admixed with 50 ng/50 µl/well of a rabbit polyclonal anti-IFNα8 antibody labelled with HRP, which had been prepared at Hayashibara Biochemical Laboratories, Inc., Okayama, Japan. Similarly as in Example 1, the resultant was subjected to coloration reaction before measurement of absorbance (OD: $A_{490}$ nm/$A_{650}$ nm) on a multi-plate reader, followed by selecting hybridomas having reactivity with rIFNα8.

EXAMPLE 3

<Preparation of Hetero Hybridoma Capable of Producing Rat-mouse>Anti-IFNα8 Antibody After kneaded with Freund's complete adjuvant, a fresh preparation of the same rIFNα8 protein as used in Experiment 1 was intraperitoneally administered to BN rats, 10-week-old, at a dose of 20 µg/head of protein, for immunization. Thereafter, the rats were further immunized twice with the same amount of the antigen as used in the above at an interval of two weeks, and further intravenously administered with the same amount at one week after the final administration. On three days after the intravenous administration, spleen was removed from each of the rats and dispersed to obtain spleen cells. The spleen cells and SP2/O—Ag14 cells (ATCC CRL1581) derived from rat myeloma were respectively suspended in RPMI1640 medium (pH 7.2) free of serum, which had been prewarmed to 37° C. at respective cell densities of $2.5 \times 10^3$ cells/ml and $5 \times 10^4$ cells/ml, and centrifuged to collect a sedimented part. To the sedimented part was dropped over one minute one milliliter of RPMI1640 (pH 7.2) free of serum but containing 50% (w/v) polyethylene glycol with an average molecular weight of 1,500 daltons, and the resulting cell suspension was incubated at 37° C. for one minute and further dropped with RPMI1640 medium (pH 7.2) free of serum until the total volume reached 50 ml, followed by centrifuging the resulting mixture to collect a sedimented part. The sedimented part was suspended in HAT medium, distributed to 96-well microplates by 200 µl/well, and incubated at 37° C. for two weeks to obtain hybridomas.

The antibody secreted in the culture supernatant in each well was assayed on an enzyme immunoassay similar to the method as in Example 1 or 2 to select hybridomas capable of producing an antibody having reactivity with rIFNα8. Subsequently, the hybridomas were repeatedly subjected to limit dilution in conventional manner to obtain clones of hybridomas, i.e., α8#S18-1 and α8#S56-1, capable of stably producing the monoclonal antibody of the present invention. The monoclonal antibodies produced by the above hybridomas can be used as antibodies for use in immunoassay for qualitative or quantitative analysis of IFNα8 and its mutant proteins, as well as in purification of such proteins. The monoclonal antibodies produced by these hybridomas can be also used intact or after prepared into chimera, humanized, or human antibodies through recombinant DNA technology, etc., as effective ingredients for therapeutic agents for diseases whose onsets or exacerbation are related with IFNα8.

EXAMPLE 4

<Preparation of Mouse Anti-IFNα8 Monoclonal Antibody>

The clones of hybridomas α8#44, α8#59, α8#98, α8#139 (deposited Feb. 15, 2008, under the terms of the Budapest Treaty in the International Patent Organism Depository (IPOD), National Institute of Advanced Industrial Science and Technology under the accession number of FERM BP-11081), and α8#145, obtained by the method in Example 1, were respectively suspended in either "HYBRIDOMA SFM COMPLETE DMP", a product name of serum-free medium commercialized by Invitrogen or RPMI1640 medium supplemented with 10% (v/v) fetal calf serum (FCS) to give a cell density of about $1 \times 10^6$ cells/ml, and successively incubated in a 5% (v/v) $CO_2$ incubator at 37° C. while scaling up their culture volumes. When reaching the desired cell density, each hybridoma was intraperitoneally injected to BALB/c mice, 8-week-old, which had been previously intraperitoneally injected with 0.5 ml/head of pristane, in a cell content of $1 \times 10^7$ cells/head, and bred for 10 days in usual manner. Ascites was collected from each rat, diluted 3-times with PBS, admixed with ammonium sulfate to give a 50% saturation, allowed to stand at 4° C. for 24 hours, and centrifuged to collect a sedimented part. The sedimented part was dialyzed, against PBS and applied to "PROTEIN G SEPHAROSE 4FF COLUMN", a product name of a protein G-bound sepharose column commercialized by GE Healthcare Biosciences, Tokyo, Japan, in usual manner to purify an IgG fraction. The anti-IFNα8 antibodies produced by the clones of hybridomas α8#44, α8#59, α8#98, α8#139 (deposited Feb. 15, 2008, under the terms of the Budapest Treaty in the International Patent Organism Depository (IPOD), National Institute of Advanced Industrial Science and Technology under the accession number of FERM BP-11081), and α8#145 are respectively called α8#44mAb, α8#59mAb, α8#98mAb, α8#139mAb, and α8#145mAb.

<Preparation of Rat or Rat-mouse Anti-IFNα8 Monoclonal Antibody>

The hybridomas α8#Y19-1 and α8Y36-2 (deposited Feb. 15, 2008, under the terms of the Budapest Treaty in the International Patent Organism Depository (IPOD), National Institute of Advanced Industrial Science and Technology under the accession number of FERM BP-11082) obtained in Example 2, and the hybridomas α8#S18-1 and α8#S56-1 obtained in Example 3 were respectively suspended in either "HYBRIDOMA SFM COMPLETE DMP", a product name of serum-free medium commercialized by Invitrogen or RPMI1640 medium supplemented with 10% (v/v) fetal calf serum (FCS) to give a cell density of about $1 \times 10^6$ cells/ml, and successively incubated in a 5% (v/v) $CO_2$ incubator at 37° C. while scaling up their culture volumes until reaching the desired culture scale. The resulting culture supernatants were respectively collected, concentrated, and applied to "PROTEIN G SEPHAROSE 4FF COLUMN", a product name of a protein G-bound sepharose column commercialized by GE Healthcare Biosciences, Tokyo, Japan, in usual manner to purify an IgG fraction produced by respective hybridomas. The anti-IFNα8 antibodies produced by the clones of hybridomas α8#Y19-1 and α8Y36-2 (deposited Feb. 15, 2008, under the terms of the Budapest Treaty in the International Patent Organism Depository (IPOD), National Institute of Advanced Industrial Science and Technology under the accession number of FERM BP-11082), α8#S18-1, and α8#S56-1 are respectively called α8#Y19-1mAb, α8#Y36-2mAb, α8#S18-1mAb, and α8#S56-1mAb.

<Characteristics of Monoclonal Antibodies>

Table 1 shows the results of the isotopes of the above-identified nine types of antibodies, which were determined on "Rat MonoAB ID kit" or "Mouse MonoAB ID kit", product names of enzyme immunoassay kits commercialized by Zymed Laboratories, CA, USA, by using a culture supernatant of each of the hybridomas cultured in a serum-free culture medium. Tables 1 and 2 show both the results of these nine types of monoclonal antibodies about their reactivity with IFNs and TNFα in Table 1 or 2, confirmed on the later described Western blotting analysis. As a representative result of Western blotting, FIG. 1 shows a pattern of Western blotting obtained by using the IFNs in FIG. 1 and a culture supernatant of α8#139. By mixing any of the culture supernatants of these hybridomas with an equal amount of a solution containing 30 to 70 IU/ml of any of the IFNs and the mutant proteins of IFNα8 shown in Table 3, the neutralization of or the activity reduction of their antiviral activity was confirmed by measuring antiviral activity with an index of cytopathic effect of Sindbis virus on FL cells. The results are in Table 3. In the Western blotting, it was judged that the reactivity was positive (+) when a TNF protein band was stained, while it was judged to be negative (−) when a TNF protein band was not stained. The neutralization activity was judged to be positive (+) when any antiviral activity was observed, while others were judged to be negative (−).

<Analysis of Western Blotting> rIFNα8 used as an antigen in Example 1 or nIFNα2 was added to a mixture solution consisting of 0.5 ml of a 10% (w/v) aqueous SDS solution and one milliliter of glycerol, and the resulting mixture was incubated at 37° C. for one hour and subjected to SDS-polyacrylamide gel electrophoresis (SDS-PAGE) after charged on the gel in an amount of 10 or 100 ng/lane of protein by weight. Proteins, contained in a part of the gel ranging from about 20 to about 29 kilo daltons (abbreviated as "kDa", hereinafter) corresponding to the molecular weights of the proteins of IFNs, were transferred to a nitrocellulose membrane and soaked in "BlockAce", a product name of a blocking solution to inhibit non-specific reaction commercialized by Dainippon Sumitomo Pharma, Co., Ltd., Tokyo, Japan. The resulting nitrocellulose membrane after the blocking treatment was soaked in a solution, containing 2 μg/ml of any of the nine monoclonal antibodies purified by using PROTEIN G SEPHAROSE, at ambient temperature for one hour, and washed with 50 mM Tris-HCl buffer (pH 7.5) containing 0.05% (v/v) tween 20 to remove excessive amounts of antibodies. The resulting nitrocellulose membrane was soaked in a solution containing an HRP labelled anti-mouse immunoglobulin or anti-rat immunoglobulin (both of which are commercialized by DakoCytomation, Denmark) at ambient temperature for one hour. The resulting membrane was washed with 50 mM Tris-HCl buffer (pH 7.5) containing 0.05% (v/v) tween 20 for 30 min and subjected to a color reaction by using commercialized "ECL western blotting detection reagent and Hyperfilm ECL", a product name of a Western blotting detection kit commercialized by GE Healthcare Biosciences, Tokyo, Japan. A commercialized molecular marker for SDS-PAGE (a product name of "PRESTEINE SDS-PAGE Standard Broadrange" commercialized by BioRad Laboratories, Inc., Tokyo, Japan) with a composition of myosin (204 kDa), β-galactosidase (120 kDa), BSA (100 kDa), ovalbumin (52 kDa), carbonic anhydrase (37 kDa), soybean trypsin inhibitor (29 kDa), lysozyme (20 kDa), and aprotinin (7 kDa) was used as a molecular marker.

As evident from Table 1, all the monoclonal antibodies obtained in Examples 1 to 3 are antibodies belonging to IgG class, whose light-chains are κ chains. Also, as evident from Tables 1 and 2, these antibodies only react with rIFNα8, nIFNα8 and two types of IFNα8 mutant proteins but not other human IFNα subtypes, IFNβ, IFNγ, Con IFN, mouse IFNα/β, rat IFNα, and TNFα, revealing that these antibodies specifically recognize IFNα8 and its mutant proteins. Further, as evident from FIG. 1, only the protein bands of nIFNα8 and rIFNα8, which had been observed at positions corresponding to molecular weights ranging from 20 to 29 kDa on Western blotting analysis, were colored but any protein bands of other IFNα were not, revealing that α8#139 mAb specifically reacts with nIFNα8 and rIFNα8 proteins. Comparing the reactivity of α8#139mAb against nIFNα8 and rIFNα8, even though equal amounts of nIFNα and rIFNα8 proteins were used in the blotting, nIFNα8 was more strongly stained than rIFNα8, confirming that the monoclonal antibody has a stronger reactivity with a natural IFNα8 than a recombinant IFNα8. Although no specific patterns of Western blotting are shown, as in Tables 1 and 2, all the antibodies produced by other eight types of hybridomas react with only natural/recombinant IFNα8 and mutant proteins of IFNα8 but not with other IFNs and TNFα. The reactivity of the above antibodies to a natural/recombinant IFNα showed a similar pattern to that of α8#139mAb. As evident from Table 3, the neutralization activity to the antiviral activity of IFNα8 was only found in α8#139mAb and α8#S56-1mAb. No neutralization activity against the antiviral activity of nIFNα2, IFNβ, and IFNγ was found in α8#139mAb and α8#S56-1mAb, revealing that these two types of monoclonal antibodies have a neutralization activity specific to IFNα8.

TABLE 1

Reactivity with human IFNα subtype or its mutant protein (Western blotting)

| X | Y | rIFNα1 | rIFNα2 | nIFNα2 | rIFNα5 | rIFNα6 | rIFNα8 | nIFNα8 | rIFNα10 | Con IFN | IFNα8-MUT2 | IFNα8-MUT3 |
|---|---|---|---|---|---|---|---|---|---|---|---|---|
| α8#44 | IgG$_1$,κ | − | − | − | − | − | + | + | − | − | + | + |
| α8#59 | IgG$_1$,κ | − | − | − | − | − | + | + | − | − | + | + |
| α8#98 | IgG$_1$,κ | − | − | − | − | − | + | + | − | − | + | + |
| α8#139 | IgG$_1$,κ | − | − | − | − | − | + | + | − | − | + | + |
| α8#145 | IgG$_1$,κ | − | − | − | − | − | + | + | − | − | + | + |
| α8#S18-1 | IgG$_1$,κ | − | − | − | − | − | + | + | − | − | + | + |
| α8#S19-1 | IgG$_1$,κ | − | − | − | − | − | + | + | − | − | + | + |
| α8#Y36-2 | IgG$_1$,κ | − | − | − | − | − | + | + | − | − | + | + |
| α8#S56-1 | IgG$_3$,κ | − | − | − | − | − | + | + | − | − | + | + |

Note:
The symbols "X" and "Y" mean "Hybridoma" and "Isotype", respectively. The symbols "+" and "−" mean "Positive reactivity" and "Negative reactivity", respectively.

TABLE 2

Reactivity with IFNs and cytokines (Western blotting)

| Hybridoma | IFNβ | IFNγ | Con IFN | Mouse IFNα/β | Rat IFNα | TNFα |
|---|---|---|---|---|---|---|
| α8#44 | − | − | − | − | − | − |
| α8#59 | − | − | − | − | − | − |
| α8#98 | − | − | − | − | − | − |
| α8#139 | − | − | − | − | − | − |
| α8#145 | − | − | − | − | − | − |
| α8#S18-1 | − | − | − | − | − | − |
| α8#Y19-1 | − | − | − | − | − | − |
| α8#Y36-2 | − | − | − | − | − | − |
| α8#S56-1 | − | − | − | − | − | − |

Note:
The symbols "+" and "−" mean "Positive reactivity" and "Negative reactivity", respectively.

TABLE 3

Neutralization activity to human IFN or its mutant (Western blotting)

| Hybridoma | nIFNα8 | rIFNα8 | IFNα8-MUT2 | IFNα8-MUT3 | rIFNα2 | IFNβ | IFNγ |
|---|---|---|---|---|---|---|---|
| α8#44 | − | − | − | − | − | − | − |
| α8#59 | − | − | − | − | − | − | − |
| α8#98 | − | − | − | − | − | − | − |
| α8#139 | + | + | + | + | − | − | − |
| α8#145 | − | − | − | − | − | − | − |
| α8#S18-1 | − | − | − | − | − | − | − |
| α8#Y19-1 | − | − | − | − | − | − | − |
| α8#Y36-2 | − | − | − | − | − | − | − |
| α8#S56-1 | + | + | + | + | − | − | − |

Note:
The symbols "+" and "−" mean "Positive neutralization activity" and "Negative neutralization activity", respectively.

EXAMPLE 5

<Construction of Enzyme Immunoassay System Against IFNα8>

Using the nine types of monoclonal antibodies prepared by the method in Example 4, screening of antibodies suitable for the construction of enzyme immunoassay system that specifically quantifies IFNα8.

<Antibody>

In this experiment, the nine types of monoclonal antibodies prepared in Example 4, as well as a rabbit polyclonal anti-IFNα antibody (abbreviated as "polyIFNα", hereinafter) and a mouse monoclonal anti-IFNα antibody (abbreviated as "mAbIFNα14", hereinafter), both of which were produced by Hayashibara Biochemical Laboratories, Inc., Okayama, Japan. The above polyIFNα and mAbIFNα14 have reactivity with IFNα8 and other human IFNα subtypes.

<Preparation of Peroxidase-labelled Antibody>

According to conventional manner, the above 11 types of antibodies were labelled with HRP by peroxidase oxidation method: Ten milligrams of HRP, commercialized by F. Hoffmann-La Roche Ltd., Swiss, was dissolved in two milliliters of distilled water, admixed with 125 μl of 0.1 M sodium periodate, and allowed to stand at ambient temperature for 15 min under light-shielded conditions. Thereafter, the mixture was admixed with 100 μl of ethylene glycol, dialyzed against 1 mM sodium acetate buffer (pH 4.2) at ambient temperature for five minutes under light-shielded conditions, and concentrated to give a concentration of HRP of 15 mg/ml or higher. Eight milligrams of HRP of the concentrate was mixed with 10 mg of any one of the 11 types of antibodies which had been concentrated to give a concentration of 20 mg/ml or higher, and the resulting mixture was volumed up to give a total volume of 850 μl by adding water, admixed with 150 μl of 0.1 M sodium bicarbonate buffer (pH 9.5), adjusted to a pH of about 9.3, and allowed to stand at 4° C. for two hours under light-shielded conditions. The mixture thus obtained was admixed with 100 μl of 4 mg/ml of sodium boron hydride, allowed to stand at ambient temperature for three hours under light-shielded conditions, and subjected to gel filtration using "Sephacryl S-300HR", a product name of gel filtration column, commercialized by EG Healthcare Bioscience, Tokyo, Japan, to collect a fraction of HPR-labelled antibody. HRP-labelled antibody (called "labelled antibody", hereinafter) was prepared by dissolving calf serum albumin (abbreviated as "BSA", hereinafter) in the above fraction to give a concentration of one percent and filtered with a membrane (pore size of 0.22 μm).

<Method of Enzyme Immunoassay>

The possibility of quantitative analysis of rIFN protein was examined with 121 combinations of enzyme immunoassays by sandwich method using, as solid-phase antibodies, the above-identified 11 types of HRP-labelled antibodies and unlabelled, intact 11 types of antibodies thereof (called "unlabelled antibodies", hereinafter). The 11 types of unlabelled antibodies were respectively diluted with PBS to give a concentration of 20 μg/ml thereof, added to an immunoplate in a volume of 50 μl/well, and allowed to stand at ambient temperature for two hours, followed by removing the solution in each well, adding PBS containing one percent of BSA to each well, and subjecting the resultant to a blocking treatment at 4° C. overnight. After the blocking treatment, the PBS containing one percent of BSA in each well was removed, and any one of the dilutions, which had been prepared by dissolving rIFNα8 in PBS containing 5% of FCS, 1% of BSA, and 1 M NaCl to give a concentration of 69 μg/ml to 60 ng/ml, was added to the resulting each well in a volume of 50 μl/well. After 2-hours shaking, each well was washed trice with PBS containing 0.05% tween 20. After removing the PBS used for washing from each well, the above-identified 11 types of labelled antibodies were diluted with PBS containing 5% FCS, 1% BSA, 0.15 M NaCl, and 0.1% CHAPS to give a concentration of 1 μg/ml, and added to the wells with the 11 types of unlabelled antibodies used as solid-phase antibodies in a volume of 50 μl/well, followed by shaking the immunoplate at ambient temperature for two hours. After removing the solution containing any of the labelled antibodies, each well was washed trice with PBS containing 0.05% tween 20, and allowed to develop color by adding 0.1 M citrate phosphate buffer (pH 5.0) containing 0.5 mg/ml of o-phenylenediamine (o-PD) and 0.03% of $H_2O_2$ in a volume of 100 μl/well, followed by suspending the reaction by the addition of 2 N $H_2SO_4$ in a volume of 100 μl/well and measuring the absorbance (OD: $A_{490/650}$ nm) for each well on a multi-plate reader. As a control, the absorbance in the case of adding PBS containing 5% FCS, 1% BSA, and 1 M NaCl but not rIFNα8 was similarly determined. For one sample, the absorbance was determined by averaging the data obtained from three wells. The lower limit of detectable concentration of rIFNα8 protein in the tested enzyme immunoassay was defined as the concentration of rIFNα8 protein with the highest value selected from among the following: A rIFNα8 protein concentration corresponding to the minimum concentration of rIFNα8 protein with a correlation coefficient (r value) of 0.997 or higher, which evaluates the linearity of calibration curve drown based on the measured absorbances by regression analysis; a value of the absorbance (OD) measured for the control well plus a value of 3-times of the standard deviation of that of the control well; and a value of the determined minimum concentration of rIFNα8 protein minus a value of 3-times of the standard deviation of that of the determined minimum concentration.

<Confirmation of Cross Reactivity with IFNα2>

An enzyme immunoassay was conducted by the same method as the above method of enzyme immunoassay except for using rIFNα2 in place of rIFNα8. It was judged that there was a positive cross reaction ("positive") when an increment of absorbance was observed depending on the concentration of rIFNα2, and there was no cross reaction ("negative") when an increment of absorbance was not observed depending on the concentration of rIFNα2.

<Results of Measurement>

Among the 121 combinations of enzyme immunoassays with the 11 types of unlabelled antibodies (as a sold phase) and the 11 types of labelled antibodies, only 14 combinations thereof, where an increment of absorbance (OD) was found depending on the concentration of rIFNα8 and a relatively low (OD of 0.4 or lower) absorbance (OD) of the solution containing 5% FCS, 1% BSA, and 1M-NaCl but not IFNα8 was found, is shown in Table 4. Among the combinations of antibodies in Table 4, it was confirmed that whether an increment of absorbance (OD) (or a positive/negative cross reaction with IFNα2) was found depending on the concentration of rIFNα2 when IFNα2 was used in place of rIFNα8. The results are shown in Table 4 in parallel. Also, Table 4 shows the lower limit of detectable concentration (pg/ml) of the 14 combinations by enzyme immunoassays, determined by the above method.

TABLE 4

| Solid-phase antibody | Labelled antibody | Cross reaction with rIFNα2 | Lower limit of detectable concentration of rIFNα8 protein | Absorbance (OD) Control (free of rIFNα8) | Absorbance (OD) rIFNα8 (50 ng/ml) |
|---|---|---|---|---|---|
| α8#59mAb | mAbIFNα14 | Negative | 617 | 0.03 | 1.0 |
|  | α8Y36-2mAb | Negative | 617 | 0.07 | 1.1 |
| α8#98mAb | polyIFNα | Negative | 1852 | 0.3 | 0.65 |
| α8#139mAb | α8Y36-2mAb | Negative | 69 or 206 | 0.05 | 3.5 |
|  | α8#44mAb | Negative | 5555 | 0.03 | 1.2 |
|  | polyIFNα | Negative | 206 | 0.2 | 2.1 |
|  | mAbIFNα14 | Negative | 69 or 206 | 0.007 | 2.7 |
| α8Y36-2mAb | α8#145mAb | Negative | 5555 | 0.05 | 0.12 |
|  | α8#139mAb | Negative | 5555 | 0.4 | 0.95 |
|  | α8#59mAb | Negative | 1852 | 0.1 | 0.9 |
|  | plyIFNα | Negative | 69 | 0.02 | 1.6 |
| α8#S56-1mAb | polyIFNα | Positive | 69> | 0.02 | 2.5 |
| polyIFNα | polyIFNα | Positive | 69 | 0.02 | 1.4 |
|  | α8#S56-1mAb | Positive | 206 | 0.2 | 1.5 |

When enzyme immunoassays were conducted with the 14 combinations of the solid-phase antibodies and labelled antibodies in Table 4, there were found increased absorptions depending on the concentration of rIFNα8. The lower limit of detectable concentration was 69 or 206 pg/ml in combinations where α8#139mAb or α8Y36-2mAb was used as a solid-phase antibody. Cross reaction with rIFNα2 was found in a combination of polyIFNα and α8#S56-1. As an enzyme immunoassay that requires specificity to IFNα8 and a relatively high detection sensitivity and measurement accuracy, a preferable combination that satisfies the requirement to be free of cross reaction with IFNα2, low in lower limit of detectable concentration of rIFNα8, and large in slope of calibration curve (being large in difference between the absorbance of control and that of IFNα8 at a concentration of 50 ng/ml) was considered to be the one constructed by using α8#139mAb as a solid-phase antibody and α8Y36-2mAb as a labelled antibody in combination, and the other constructed by using α8Y36-2mAb as a solid-phase antibody and polyIFNα as a labelled antibody. These results indicate that assay systems, which specifically detect IFNα8 at a relatively high sensitivity, can be constructed by using α8#139mAb or α8Y36-2mAb, as a solid-phase, which specifically recognizes IFNα8. Considering a possible reactivity of mAb-IFNα14 or polyIFNα with IFNα subtypes other than IFNα8 when these antibodies are used as labelled antibodies, it was judged that, as an enzyme immunoassay system specific to IFNα8 subtype, a combination use of α8#139mAb as a solid-phase antibody and α8Y36-2mAb as a labelled antibody is particularly preferable.

EXAMPLE 6

<Detectable Range of IFNα8 by Enzyme Immunoassay System Specific to IFNα8 Subtype>

Figure 2:
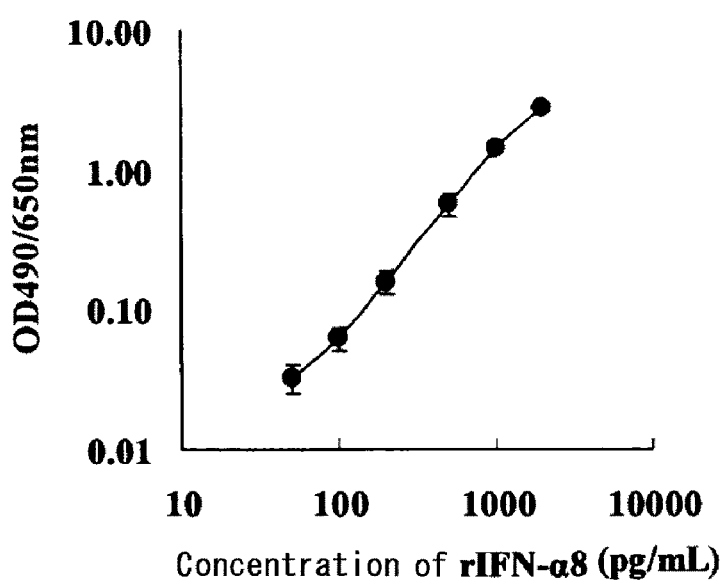
FIG. 2 is a figure for explaining an example of standard curve of rIFNα8 determined on an enzyme immunoassay in a sandwich method where the monoclonal antibodies α8#139mAb and α8Y36-2mAb were respectively used as a solid-phase antibody and a labelled antibody.

According to the later described method, an enzyme immunoassay was conducted by using α8#139mAb as a solid-phase antibody and α8Y36-2mAb as a labelled antibody, which had been judged to be usable for specific detection of IFNα8 in Example 5, and the result of a calibration curve for rIFNα8 is shown in FIG. 2. The lower limit of detectable concentration of IFNα8 protein in the enzyme immunoassay system, calculated based on the above calibration curve, was determined based on the method disclosed in Example 5 and was shown in Table 5 in parallel. Table 5 also shows the upper limit of detectable concentration of rIFNα8 protein obtained by the enzyme immunoassay in such a manner of determining the maximum concentration of rIFNα8 protein corresponding to the maximum OD value within the range having a correlation coefficient (r-value) of 0.997 or higher as a linearity of the calibration curve.

<Confirmation of Specificity of Enzyme Immunoassay Specific to IFNα8 Subtype>

To confirm that the enzyme immunoassay system, where α8#139mAb and α8Y36-2mAb are respectively used as a solid-phase antibody and a labelled antibody, does not detect IFNs other than IFNα8 and cytokine proteins, the results of measurements of absorbances obtained by assaying the IFNs and cytokines with the protein concentrations in Table 5 are shown in the table in parallel.

<Method of Enzyme Immunoassay>

α8#139mAb as a solid-phase antibody was diluted with PBS into a 20 μg/ml solution, and the solution was distributed to an immunoplate commercialized by Nunc Roskilde, Denmark, by 100 μl/well. After 3-hours standing at ambient temperature, the solid-phase solution was removed from each well, and PBS containing one percent of BSA was added to the immunoplate by 250 μl/well, followed by allowing the immunoplate to stand at 4° C. overnight for blocking. The PBS was removed from each well, and rIFNα8 was prepared into solutions as standard specimens with concentrations of 10 to 2,000 pg/ml by diluting with PBS containing 2.5% of FCS, 0.5% of BSA, and 0.5M NaCl. By using as test samples the IFNs or cytokines in Table 5, they were respectively diluted with a fresh preparation of the same PBS containing FCS, BSA and NaCl as used in the dilution of IFNα8 into solutions with a concentration of 10 ng/ml, and any one of which was added to an immunoplate by 100 μl/well, followed by shaking the immunoplate for three hours. Thereafter, the standard specimen solution or the solutions with the test samples were removed from each well, and the wells were washed trice with PBS containing 0.05% of tween 20. After removing the washing solution, one microgram per milliliter of HRP-labelled α8Y36-2mAb, which had been prepared by diluting with PBS containing 5% of FCS, 1% of BSA, 0.15M NaCl, and 0.1% of CHAPS, was added to the immunoplate by 100 μl/well. The immunoplate was shaken at ambient temperature for two hours and each well thereof was washed trice with PBS containing 0.05% of tween 20. After removing the solution used for washing, 0.1 M citrate phosphate buffer (pH 5.0) containing 0.5 mg/ml of o-PD and 0.03% of $H_2O_2$ was added to the immunoplate in an amount of 100 μl/well to develop color, followed by adding 2 N $H_2SO_4$ to the immunoplate in an amount of 100 μl/well to suspend the coloration reaction and measuring the absorbance (OD: $A_{490/650}$) for each well by a multiplate reader. For each sample, three wells were used for the above measurement, and the data were averaged.

TABLE 5

| IFNs/Cytokines | Specific activity (IU or U/mg protein) | Protein concentration (ng/ml) | Absorbance (OD) |
|---|---|---|---|
| rIFNα1 | $7.55 \times 10^6$ | 10 | 0.014 |
| rIFNα2 | $1.68 \times 10^8$ | 10 | 0.013 |
| nIFNα2 | $1.82 \times 10^8$ | 10 | 0.011 |
| rIFNα5 | $3.91 \times 10^7$ | 10 | 0.010 |
| rIFNα6 | $5.35 \times 10^7$ | 10 | 0.024 |
| rIFNα8 | $2.49 \times 10^8$ | 2 | 2.991 |
| nIFNα8 | $2.98 \times 10^8$ | 2 | 2.910 |
| rIFNα10 | $1.41 \times 10^8$ | 10 | 0.010 |
| Con IFN | $1 \times 10^9$ | 10 | 0.009 |
| IFNβ | $2 \times 10^8$ | 10 | 0.013 |
| IFNγ | $1.46 \times 10^7$ | 10 | 0.010 |
| TNFα | $9.37 \times 10^8$ | 10 | 0.010 |
| Rat IFNα | $2.97 \times 10^7$ | 10 | 0.009 |
| Mouse IFNα/β | $1.38 \times 10^7$ | 10 | 0.011 |
| IFNα8-MUT2 | $4.2 \times 10^8$ | 2 | 3.079 |
| IFNα8-MUT3 | $3.9 \times 10^8$ | 2 | 2.604 |
| rIFNα8 (Detectable upper-limit concentration) | — | 2 | 2.991 |
| rIFNα8 (Detectable lower limit concentration) | — | 0.05 | 0.033 |
| Buffer alone | — | 0 | 0.015 |

As evident from FIG. 2, in the enzyme immunoassay using α8#139mAb as a solid-phase antibody and α8Y36-2mAb as a labelled antibody according to the above conditions, it was observed a linear increment of absorbance proportional to the protein amount in the range of 0.05 to 2 ng/ml (50 to 2,000 μg/ml) of rIFNα8. The result indicates that the enzyme immunoassay system accurately detects at least about 50 to about 2,000 pg/ml of the protein. As evident from Table 5, even when anyone of IFNα subtypes other than nIFNα8 including rIFNα8 and its mutants, IFNβ, IFNγ, Con IFN, rat IFNα, mouse IFNα/β, and TNFα was assayed after prepared into a solution containing 10 ng/ml thereof which corresponds to 200 times of the detectable lower-limit concentration of IFNα8 (5 times of the detectable upper-limit concentration of IFNα8), the absorbances thereof had no difference compared to that with buffer alone used for dissolving these proteins. The result indicates that the enzyme immunoassay has successfully constructed an enzyme immunoassay system specific to IFNα8 and its mutants without cross reaction with cytokines and IFNs other than IFNα8 and its mutants.

EXAMPLE 7

<Detection of rIFNα8 Protein by Radioimmunoassay>

According to conventional manner, solid-phase antibody beads were prepared by adsorbing α8#139mAb on polyethylene beads for radioimmunoassay in conventional manner and allowing the beads to stand in PBS containing 2% (w/v) of BSA at 4° C. overnight.

The solid-phase antibody beads were respectively placed in test tubes one by one; received with the rIFNα8 used in Example 1, which had been diluted with PBS containing 0.5% (w/v) of BSA into a solution with an appropriate concentration, by 0.2 ml; and allowed to stand at 4° C. for four hours. The resulting solid-phase antibody beads were washed with PBS containing 0.05% (v/v) of tween 20 and 0.5% (w/v) of BSA; received with α8Y36-2 mAb obtained by the method in Example 4, which had been labelled with $^{125}$I in conventional manner by 0.2 ml ($1 \times 10^5$ cpm); and allowed to stand at 4° C. overnight. After removing the excessive amounts of the labelled antibodies, the resulting beads were washed with PBS containing 0.05% (v/v) of tween 20 and 0.5% (w/v) of BSA, and determined for radioactivity on a gamma counter to accurately detect 10 to 1,000 pg/ml of IFNα8 and its mutant proteins.

EXAMPLE 8

<Quantification of Human IFNα8 Protein Derived from Ball-1 Cells on Enzyme Immunoassay>

It is known that nIFNα induced by adding HVJ to BALL-1 cells, a human lymphoblastoid cell line (possessed by Hayashibara Biochemical Laboratories, Inc., Okayama, Japan) contains nIFNα2 and nIFNα8 (IFNα8b) in a weight ratio of 72±9:28±9 and a slight amount of nIFNα7 (see, for example, Shigeharu Fukuda et al., *Lymphokine*, Vol. 7, No. 2, pp. 175-185, 1988). The following experiment was done to confirm that the enzyme immunoassay system of the present invention used in Example 6 specifically quantifies nIFNα8 in the human nIFNα derived from BALL-1 cells: BALL-1 cells were subcutaneously transplanted to the dorsal part of a new born hamster, and then the proliferated cells were suspended in RPMI1640 medium and allowed to stand overnight after adding HVJ to the supernatant. Both a solution prepared by irradiating the resulting supernatant with ultraviolet ray to inactivate the HVJ (abbreviated as "BALL-1 culture supernatant", hereinafter) and a human nIFNα specimen prepared by purifying the solution with a column of "NK2-SEPHAROSE", a product name of a monoclonal antibody commercialized by Lonza Japan, Tokyo, Japan, were subjected to a bioassay and an enzyme immunoassay specific to IFNα2 and IFNα8. The results are in Table 6. In the bioassay, the result of the determined activity for a specimen, in which nIFNα8 had been previously specifically neutralized by the addition of the anti-IFNα8 antibody (α8#139mAb) prepared in Example 4, was shown in Table 6 in parallel. In the enzyme immunoassay for quantifying nIFNα8, the assay system constructed in Example 6 was used, while nIFNα2 was assayed using "Human IFN-α Assay Kit", a product name of an IFNα assay kit commercialized by JIMRO Co., Ltd., Tokyo, Japan. For one sample three wells were used and the data were averaged.

TABLE 6

| | Anti-viral Activity | BALL-1 cell culture supernatant | Human nIFNα purified on antibody column |
|---|---|---|---|
| X | Total activity (IU/ml) | $3.08 \times 10^4$ | $4.4 \times 10^7$ |
| | nIFNα2 (IU/ml)*[1] | $1.93 \times 10^4$ | $2.77 \times 10^7$ |
| | nIFNα8 (IU/ml)*[2] | $1.16 \times 10^4$ | $1.63 \times 10^7$ |
| | nIFNα8/Total human nIFNα (%) | 37.7 | 37.0 |
| Y | Total content (ng/ml) | 107.0 | 173000 |
| | nIFNα2 (ng/ml) | 64.5 | 117000 |
| | nIFNα8 (ng/ml) | 42.5 | 56000 |
| | nIFNα8/Total human nIFNα (%) | 39.7 | 32.4 |

Note:
The symbol "*1" means "activity after neutralization with anti-IFNα8 antibody".
The symbol "*2" means "an activity corresponding to {(Total IFNα activity) − (activity after neutralization with anti-IFNα8 antibody)}".
The symbols "X" and "Y" mean "Bioassay" and "Enzyme immunoassay", respectively.

As evident from Table 6, the bioassay revealed that about 38% of the total human IFNα activity of the human nIFNα contained in the BALL-1 culture supernatant was calculated to be of nIFNα8. When a fresh preparation of the same culture supernatant as used in the above was determined on the enzyme immunoassay specific to nIFNα2 and nIFNα8, about 40% of the total human IFNα activity was calculated to be of nIFNα8. In the specimen prepared by purifying the BALL-1 culture supernatant with the antibody column, the bioassay revealed that about 37% of the total human IFNα activity was calculated to be of IFNα8. When a fresh preparation of the same culture supernatant as used in the above was determined on the enzyme immunoassay specific to nIFNα2 and nIFNα8, about 32% of the total human IFNα activity was calculated to be of nIFNα8. It was judged that the percentage (%) of IFNα8 accounting for the total human IFNα activity was well coincided with authentic values and with the result of the above bioassay, considering the error in the measurement for activity by the bioassay. Not showing in the table, the Bradford method for measuring protein content of a specimen purified on a commercialized antibody column (NK2-Sepharose column), i.e., a human nIFNα purified on an antibody column, gave 184.9 µg/ml, and this value almost coincided with 173 µg/ml of the total amount of proteins of the nIFNα2 and nIFNα8 obtained through calculation based on the result of the enzyme immunoassay. These results indicate that the enzyme immunoassay system using the monoclonal antibody of the present invention specifically determines the content of IFNα8 protein, while having a well correlation with the results of bioassay.

EXAMPLE 9

<Pharmacokinetics of Human nIFNα (Derived from Ball-1 Cells) and nIFNα8>

A human nIFNα (containing 6.46 µg of nIFNα and 1.81 µg of nIFNα8), the IFNα8-MUT2 (containing 5.83 µg) used in Example 6, or IFNα8-MUT3 (containing 5.38 µg) was subcutaneously administered to four BALB/c mice (female, 9-week-old, commercialized by Charles River Laboratories Japan, Inc., Tokyo, Japan) at a dose of about $10^6$ IU/head. After the administration, the mice were sampled blood from their tail veins in a time-dependent manner (at 0, 0.5, 1, 2, 3, 6 and 24 hours after the administration) and centrifuged to obtain sera, followed by subjecting the sera to the same enzyme immunoassay specific to IFNα2 and IFNα8 as used in Example 8. Based on the results of the measurements, AUC (area under the blood concentration-time curve), MRT (mean resistant time), Cmax (maximum drug concentration), Tmax (maximum drug concentration time), and EBA (extent of bioavailability) were determined for each mouse when administered with any of the IFNα8 and its mutant proteins, followed by averaging the data to show in Table 7. For measurement, three wells were used for each sample and the data were averaged.

TABLE 7

| Type of human IFNα | Human nIFNα | | | |
|---|---|---|---|---|
| Subtype | nIFNα2 | nIFNα8 | IFNα8-MUT2 | IFNα8-MUT3 |
| Dose (ng) | 6460 | 1810 | 5830 | 5380 |
| AUC (ng · time/ml) | 553 | 1975 | 917 | 562 |
| MRT (hour) | 2.4 | 3.9 | 2.2 | 2.0 |
| Cmax (ng/ml) | 188 | 313 | 311 | 212 |

TABLE 7-continued

| Type of human IFNα | Human nIFNα | | | |
|---|---|---|---|---|
| Subtype | nIFNα2 | nIFNα8 | IFNα8-MUT2 | IFNα8-MUT3 |
| Tmax (hour) | 1 | 1 | 0.8 | 0 |
| EBA (%) | 8.6 | 109 | 15.7 | 10.4 |

As evident from Table 7, the amount of nIFNα8 contained in human nIFNα was less than 1/3 of nIFNα2, however, nIFNα8 had a 3.6 (≈1975/553) times higher AUC as a pharmacokinetic factor than that of nIFNα2 and also had a 1.7 (≈3.9/2.4) times higher MRT. It was also revealed that the blood dynamics of the mutant proteins of IFNα8 resembled to that of nIFNα2 rather than nIFNα8 in terms of MRT and EBA. These results indicate that the enzyme immunoassay system specific to IFNα8 of the present invention is a more appropriate assaying method than bioassay for monitoring the in vivo dynamics of IFNα8 and its mutant proteins and their movement in living bodies such as distribution/excretion.

EXAMPLE 10

<Preparation of Gel for Immunoaffinity Chromatography>

A purified specimen of α8#139mAb obtained by the method in Example 4 was weighed in an amount of 80 mg and dialyzed against 0.1 M borate buffer (pH 8.5) containing 0.5 M sodium chloride at 4° C. overnight. Four grams of "CNBr-ACTIVATED SEPHAROSE 4B", a product name of a water-insoluble carrier commercialized by GE Healthcare Biosciences, Tokyo, Japan, was allowed to swell in 1 mM aqueous hydrochloric acid solution, washed successively with a fresh preparation of 1 mM aqueous hydrochloric acid solution and 0.1 M borate buffer (pH 8.5) containing 0.5 M sodium chloride, and admixed with about 10 ml of the above aqueous solution of monoclonal antibody, followed by gently stirring at ambient temperature for two hours and further at 4° C. overnight. Thereafter, the resulting gel was successively washed with 1 M aqueous ethanol amine solution (pH 8.0), 0.1 M borate buffer (pH 8.5) containing 0.5 M sodium chloride, and 0.1 M acetate buffer (pH 4.0) containing 0.5 M sodium chloride, and the above washing step was repeated five times. Finally, the resulting gel was washed with PBS to obtain a gel for immunoaffinity chromatography. Conventional analysis of the gel revealed that about six milligrams of the monoclonal antibody, α8#139 mAb, bound to one milliliter of the gel.

EXAMPLE 11

<Purification of nIFNα8 on Immunoaffinity Chromatography>

Ten milliliters of the gel for immunoaffinity chromatography obtained in Example 10 was packed in a cylindrical plastic tube to form a column, washed with PBS, and, according to the method disclosed in Japanese Patent No. 112301, applied with a 40 ml fraction containing about 0.1 mg/ml of a human nIFNα produced by adding HVJ to BALL-1 cells, which had been proliferated in immunosuppressed hamsters by transplanting seed cells thereof to the hamsters. After washing with a fresh preparation of PBS, the column was fed with 0.1 M citrate buffer (pH 1.9) containing 0.3 M sodium chloride to collect fractions with anti-viral activity. The collected fractions were pooled, concentrated, and assayed for protein content, revealing that a purified protein with a purity of 99.8% or higher was obtained. When the purified protein was subjected to the enzyme immunoassay specific to the IFNα2 or IFNα8 used in Example 8, IFNα2 protein was not detected but only IFNα8 protein. It was revealed that the antibody column is suitable for purifying IFNα8 based on the following reasons: Considering the specific activity of nIFNα8, the protein amount of the assayed IFNα8 well correlates with the anti-viral activity of the purified IFNα8 protein, and the nIFNα8 contained in the human nIFNα, which had been applied to the column, was almost completely recovered.

EXAMPLE 12

<Cloning of cDNA Fragment of a Region of the Heavy- and Light-chains Variable Regions of Monoclonal Antibody Produced by α8#139, and Identification of the Nucleotide Sequence of the cDNA Fragment>

The following are the cloning of a cDNA fragment of a region containing the heavy- and light-chains variable sites of a monoclonal antibody produced by α8#139, a monoclonal antibody, i.e., α8#139mAb, produced by α8#139 (deposited Feb. 15, 2008, under the terms of the Budapest Treaty in the International Patent Organism Depositary (IPOD), National Institute of Advanced Industrial Science and Technology under the accession number of FERM BP-11081), and identification of the nucleotide sequence (including the amino acid sequence) of the cDNA fragment.

<Extraction of RNA>

About $3 \times 10^6$ cells of α8#139 was prepared by culturing the α8#139 in conventional manner. Using "RNeasy Mini Kit (Cat. No. 74104)", a product name of a commercialized RNA preparation kit commercialized by QIAGEN K. K., Tokyo, Japan, and according to the description of "Purification of total RNAs from animal cells with centrifugation" in the specification attached to the kit, 30 to 60 μg of RNAs were obtained by extracting the RNAs from a cell homogenate. To prepare the cell homogenate, "QIAshredder Spin Column", a product name of a column commercialized by QIAGEN K. K., Tokyo, Japan, was not conducted with DNAaseI treatment.

<Reverse Transcriptase Reaction and PCR Reaction>

As reverse transcriptase reaction and PCR reaction, a reverse transcriptase reaction was conducted by using "Superscript III Reverse Transcriptase (Cat. No. 18080-044)", a product name of a commercialized kit commercialized by Invitrogen Corp., USA, and using, as a primer, a commercialized oligo $(dT)_{12-18}$ (Cat. No. 18418-012, commercialized by Invitrogen Corp., USA) according to the description of the handling manual, "First Strand cDNA Synthesis". PCR reaction was done by using the resulting cDNA as a template and a commercialized "Mouse Ig-Primer Set" (Cat. No. #69831-3, commercialized by Novagen Inc., South Africa) as a primer. A commercialized "KOD-Plus-(Cat. No. KOD-201)", a product name of a kit produced by TOYOBO Co., Ltd., Tokyo, Japan (called "KOD Kit", hereinafter) was used a DNA polymerase. When a desired amplification was unsuccessful with KOD Kit, "TaKaRa Ex Taq (code RR001A), called "Ex Taq Kit, hereinafter", a product name of a kit produced by Takara Bio Inc., Tokyo, Japan, was used instead. In the Mouse Ig-Primer Set, six primers of "MuIg-$GV_H$ 5' A-F" as 5'-primers and one primer of "MuIgGV$_H$ 3'-2" as a 3'-primer were used in combination for PCR reaction to amplify the DNA of the heavy-chain variable region of α8#139mAb. To amplify the light-chain variable region of α8#139mAb, seven primers of "MuIgκV$_H$5' A-G" as 5'-primers and one primer of "MuIgκV$_L$3'-1" as a 3'-primer were used. All the 5'-primers used were those which contain a nucleotide sequence with an initiation codon. The following are the reaction conditions for use in the KOD kit and the Ex Taq kit:

| <Reaction conditions for KOD kit> | |
|---|---|
| KOD-Plus-(1 U/μl) | 0.5 μl |
| 10 x PCR Buffer | 2.5 μl |
| 25 mM MgSO$_4$ | 1 μl |
| 2 mM dNTPs | 2.5 μl |
| Template for post reverse transcriptase reaction | 1 μl |
| 5'-Primer: | |
| For 5' A and B primers or | 12.5 pmol |
| For 5' C-G primer | 5 pmol |
| 3'-Primer | 2.5 pmol |

Adequate amount of distilled water sufficient to make a total volume of 25 μl/tube.

The tube is subjected to a successive three-different-temperature-cycle of 94° C. for two minutes, 94° C. for 15 sec, X° C. for 30 sec, and 68° C. for one minute, which is repeated 30 to 40 times before the tube is cooled to 4° C.

Note: "X" means 50° C. for 5' A and B Leader primers and 60° C. for 5' C-G Leader primer.

| <Reaction conditions for Ex Taq kit> | |
|---|---|
| Ex Taq (5 U/μl) | 0.25 μl |
| 10 x Ex Taq PCR Buffer | 5 μl |
| 2.5 mM dNTPs | 4 μl |
| Template for post reverse transcriptase reaction | 1 μl |
| 5'-Primer: | |
| For 5' A and B primers or | 25 pmol |
| For 5' C-G primer | 10 pmol |
| 3'-Primer | 5 pmol |

Adequate amount of distilled water sufficient to make a total volume of 50 μl/tube.

The tube is subjected to a successive three-different-temperature-cycle of 94° C. for one minute, Y° C. for one minute, and 72° C. for one minute, which is repeated 30 to 35 times before the tube is cooled to 4° C.

Note: "Y" means 50° C. for 5' A and B Leader primers and 60° C. for 5' C-G Leader primer.

<Preparation of DNA Fragment>

The PCR reaction solutions with amplified DNAs of the above heavy- and light-chains variable regions were respectively subjected to agarose electrophoresis and to either "QIAEX II Gel Extraction Kit", a product name of a commercialized kit produced by QIAGEN K. K., Tokyo, Japan, with reference to "QIAEX II Agarose Gel Extraction Protocol" in the specification; or "StrataPrep PCR Purification Kit" contained in "PCR-Script Cam Cloning Kit (#211192)", a product name of a commercialized kit commercialized by Stratagene, USA, with reference to the specification, "Purifying the PCR Products with the StrataPrep PCR Purification Kit", resulting in purification of PCR amplified fragments in the post PCR reaction solution from the gel containing amplified DNA fragments with about 500 bp. The DNA fragments amplified with the Ex Taq kit were blunted according to "Polishing the Purified PCR Products" as a manual for handling of "PCR-Script Cam Cloning Kit" produced by Stratagene, USA.

<Transformation and Screening>

The purified DNA fragments thus obtained were ligated to pPCR-Script Cam SK(+)Vector using "PCR-Script Cam Cloning Kit (#211192)" produced by Stratagene, USA, and used to transform "Competent Cell XL10-Gold" in the kit. The resultants were inoculated to a plate containing X-gal, chloramphenicol, and IPTG, followed by picking up white colonies and selecting clones with a desired-sized insert from the colonies by colony direct PCR method. From cultures of colonies with a desired-sized fragment, plasmids were prepared using "QIAprep spin Miniprep Kit (Cat. No. 27106)", a product name of a commercialized plasmid preparation kit commercialized by QIAGEN K. K., Tokyo, Japan. The reaction conditions of the colony direct method are as follows:

| <Reaction conditions of colony direct PCR method> | |
|---|---|
| Ex Taq (5 U/μl) | 0.05 μl |
| 10 x Ex Taq PCR Buffer | 1μ |
| 2.5 mM dNTPs | 0.8 μl |
| T3 Primer | 10 ng |
| T7 Primer | 10 ng |

The above mixture is admixed with distilled water to make a total volume of 10 μl/tube.

The reaction solution in the tube is mixed with a replica collected in the form of a tip-stuck colony.

The resulting tube is subjected to a successive three-different-temperature-cycle of 94° C. for one minute, 55° C. for one minute, and 72° C. for one minute, which is repeated 30 to 35 times before the tube is cooled to 4° C.

<Sequence>

The nucleotide sequences of DNAs were determined by sequencing from the both ends of each DNA using a vector T3 primer (5'AATTAACCCTCACTAAAGGG3': SEQ ID NO: 1) and T7 primer (5'GTAATACGACTCACTATAGGGC3': SEQ ID NO: 2) by means of "CEQ8000", a product name of an automatic DNA sequencer commercialized by Beckman Coulter Inc., USA, to obtain three clones with a DNA encoding a heavy-chain variable region and three clones with a DNA encoding a light-chain variable region. Among the three clones with the DNA encoding the heavy-chain variable region, two clones had the nucleotide sequence of SEQ ID NO: 3, and the remaining one clone had the nucleotide sequence of SEQ ID NO: 4. All the three clones, which contain the nucleotide sequence for the light-chain variable region, had the nucleotide sequence of SEQ ID NO: 5.

<Amino Acid Sequence>

The amino acid sequences of SEQ ID NOs: 6 to 8 respectively show the results of the amino acid sequences containing the heavy- and light-chains variable regions of α8#139mAb that follow the amino acid sequence of the 5'-primer part used in their clonings, which were estimated based on the nucleotide sequences of the above three DNAs. Based on the known amino acid sequences of the N-termini of heavy- and light-chains constant regions, the amino acids of the C-termini of heavy- and light-chains were determined and the amino acid sequences of the heavy- and light-chains variable regions of α8#139mAb were determined. The above respective amino acid sequences are shown in SEQ ID NOs: 9 to 11. The amino acid sequence of SEQ ID NO: 10 contained the one of SEQ ID NO: 9, where the 37th phenylalanine (Phe) positioning from the N-terminus had been replaced with isoleucine (Ile) and the 79th isoleucine (Ile) had been replaced with threonine (Thr). Considering the number of the obtained clones, the amino acid sequence of the heavy-chain variable region of α8#139mAb has the amino acid sequence of SEQ ID NO: 9 and some of the antibodies have the amino acid sequence of SEQ ID NO: 10.

EXAMPLE 13

<Cloning of cDNA Fragments of the Heavy- and Light-chains Variable Regions of Monoclonal Antibody Produced by α8Y36-2 and the Identification of the Nucleotide Sequences Thereof>

Cloning of cDNA fragments of the heavy- and light-chains variable regions of a monoclonal antibody, α8Y36-2mAb, produced by α8Y36-2 (deposited in National Institute of Bioscience and Human-Technology Agency of Industrial Science and Technology under the accession number of FERM BP-11082) and the identification of the nucleotide sequences thereof (including the amino acid sequences) were conducted as follows: α8Y36-2 was cultured in conventional manner to prepare about $3 \times 10^6$ cells thereof. Handling after the RNA extraction were the same methods as in Example 12. Three clones which contain a DNA encoding the heavy-chain variable region and two clones which contain a DNA encoding the light-chain variable region were obtained and determined for the nucleotide sequences of the DNAs. Among the three clones which contain the DNA encoding the heavy-chain variable region, two clones had the nucleotide sequence of SEQ ID NO: 12, and the remaining one clone had the nucleotide sequence of SEQ ID NO: 13. Both of the two clones, which contain the nucleotide sequence of the light-chain variable region, had the nucleotide sequence of SEQ ID NO: 14.

<Amino Acid Sequence>

The amino acid sequences of SEQ ID NOs: 15 to 17 are respectively the results on the amino acid sequences estimated based on the nucleotide sequences of the above three DNAs, where the above amino acid sequences contain the heavy- and light-chains variable regions of α8Y36-2mAb and follow the amino acid sequence of the 5'-primer part used in their clonings. Based on the known amino acid sequences of the N-termini of the heavy- and light-chains constant regions, the amino acids of the C-termini of the heavy- and light-chains were determined and the amino acid sequences of the heavy- and light-chains variable regions of α8Y36-2mAb were determined to respectively shown in SEQ ID NOs: 18 to 20. The amino acid sequence of SEQ ID NO: 19 had the one of SEQ ID NO: 18, where the 19th glycine (Gly) had been replaced with aspartic acid (Asp). Considering the number of the obtained clones, the amino acid sequence of the heavy-chain variable region of α8Y36-2mAb is speculated to have the amino acid sequence of SEQ ID NO: 18 and some of the antibodies are speculated to have the amino acid sequence of SEQ ID NO: 19.

The results in Examples 12 and 13 indicate that chimera-, humanized-, and human-antibodies, which specifically recognize human IFNα8 and its mutant proteins and which are used for quantitative/qualitative analyses and purification of IFNα8 and used as therapeutic agents for IFNα8-related diseases, clinical diagnostic agents, etc., can be advantageously prepared by practicing conventional methods (see, for example, Japanese Patent Kokai Nos. 2004-533217 and 2007-252372) in such a manner of using the whole or a part of the nucleotide sequences of the DNAs of the heavy- and light-chains variable sites of α8#139mAb and α8Y36-2mAb, and the amino acid sequences thereof; or making recombinant transformants thereof through modification of deletion, addition, replacement, etc., of 1 to about 100 amino acids in or to the above amino acid sequences.

The amino acid sequences of hypervariable sites, which exist at three positions in both the heavy- and light-chains variable regions of α8#139mAb and α8Y36-2mAb, respectively, were determined based on the amino acid sequences of the heavy- and light-chains variable sites of the α8#139mAb and α8Y36-2mAb obtained in Examples 12 and 13 by applying the method of Kabat et al. (see, for example, published by NIH, Vol. I, No. 91-3242, pp. 647-669, 1991). It was revealed that the hypervariable sites of the heavy-chains of α8#139mAb have the amino acid sequences of SEQ ID NOs: 21 to 23, respectively, while the hypervariable sites of the light-chain of α8#139mAb have the amino acid sequences of SEQ ID NOs: 24 to 26, respectively. It was also revealed that the hypervariable sites of the heavy- and light-chains variable sites of α8Y36-2mAb are the amino acid sequences of SEQ ID NOs: 27 to 29, respectively, while the hypervariable sites of the light-chain of α8#139mAb are the amino acid sequences of SEQ ID NOs: 30 to 32, respectively. These results indicate that chimera-, humanized-, and human-antibodies, which specifically recognize human IFNα8 and its mutant proteins and which are used for quantitative/qualitative analyses and purification of IFNα8 and used as therapeutic agents for IFNα8-related diseases, clinical diagnostic agents, etc., can be advantageously prepared by using the nucleotide sequences of the DNAs of the hypervariable sites, which are possessed by the heavy- and light-chains of α8#139mAb and α8Y36-2mAb and regulate their antibodies' specificities; and making recombinant transformants thereof through modification of deletion, addition, or replacement of 1 to about 100 amino acids in or to the above amino acid sequences.

EXAMPLE 14

<Therapeutic Agent>

Any of the nine types of monoclonal antibodies prepared by the method in Example 4, α,α-trehalose (free of pyrogen, produced by Hayashibara Biochemical Laboratories, Inc., Okayama, Japan), L-histidine chloride, L-histidine, and tween 20 were respectively dissolved in refined water to give concentrations of 150 mg/ml, 140 mg/ml, 3.4 mg/ml, 2.2 mg/ml, and 0.6 mg/ml. One milliliter aliquots of the resulting solution were respectively distributed to vials and prepared in conventional manner into 9-types of lyophilized preparations for injection use. In use, the products can be used as an injection agent after dissolving in physiological saline. The products are useful as therapeutic agents for diseases whose onsets or exacerbation are related with IFNα8. These nine types of lyophilized preparations were respectively dissolved in physiological saline and then intraperitoneally administered to five rats (with an average body weight of 123 g/head) at a dose of 5 ml/head (750 mg/head/shot as a dose of monoclonal antibody) once a day for successive seven days, while the rats were weighed every day. As a control, a physiological saline was intraperitoneally administered to five rats (with an average body weight of 127 g/head) at a dose of 5 ml/head once a day for successive seven days, while the rats were weighed every day. Comparing the body weights of the rats administered with the preparations with those of the control rats, no difference was found between the rats with any of the preparations and the control rats. Also there was found no apparent abnormality in the rats administered with the preparations and in the control rats.

EXAMPLE 15

<Therapeutic Agent>

Based on the nucleotide sequences (SEQ ID NOs: 3 to 5) encoding regions containing the heavy- and light-chains variable sites of the α8#139mAb obtained in Example 12, and, based on the amino acid sequences (SEQ ID NOs: 9 to 11) of the variable sites, a humanized antibody was prepared in conventional manner and purified to a level with a purity of 99.98% or higher. The antibody thus obtained, α,α-trehalose (a pyrogen-free α,α-trehalose produced by Hayashibara Biochemical Laboratories, Inc., Okayama, Japan), L-histidine chloride, L-histidine, and tween 20 were dissolved in refined water to give respective concentrations of 200 mg/ml, 140 mg/ml, 3.4 mg/ml, 2.2 mg/ml, and 0.6 mg/ml, followed by distributing the solution into vials by one milliliter and lyophilizing the resulting solution in each vial to obtain a lyophilized preparation. In use, the product can be dissolved in physiological saline into an injection for use. The product is useful as a therapeutic agent for diseases whose onsets or exacerbation are related with IFNα8. After the product was dissolved in physiological saline, the resulting solution was intravenously administered to five mice (an average body weight of 23 g/head) at a dose of 0.5 ml/head (100 mg/head/shot as a dose of monoclonal antibody) once a day for successive seven days, while the mice were weighed every day. As a control, a physiological saline was administered to five mice (with an average body weight of 24 g/head) at a dose of 0.5 ml/head once a day for successive seven days, while the mice were weighed every day. Comparing the body weights of the mice administered with the above solution with those of the control mice, no difference was found between them. Also there was found no apparent abnormality in the mice administered with the above solution and in the control mice.

EXAMPLE 16

<Therapeutic Agent>

Based on the nucleotide sequences (SEQ ID NOs:12 to 14) encoding regions containing the heavy- and light-chains variable sites of the α8Y36-2mAb obtained in Example 13, and, based on the amino acid sequences (SEQ ID NOs: 18 to 20) of the regions, a humanized antibody was prepared in conventional manner and purified to a level with a purity of 99.98% or higher. The antibody thus obtained, α,α-trehalose (a pyrogen-free α,α-trehalose produced by Hayashibara Biochemical Laboratories, Inc., Okayama, Japan), L-histidine chloride, L-histidine, and tween 20 were dissolved in refined water to give respective concentrations of 200 mg/ml, 140 mg/ml, 3.4 mg/ml, 2.2 mg/ml, and 0.6 mg/ml, followed by distributing the solution into vials by one milliliter and lyophilizing the resulting solution in each vial to obtain a lyophilized preparation. In use, the product can be dissolved in physiological saline into an injection for use. The product is useful as a therapeutic agent for diseases whose onsets or exacerbation are related with IFNα8. After the product was dissolving in physiological saline, the resulting solution was intravenously administered to five mice (an average body weight of 23 g/head) at a dose of 0.5 ml/head (100 mg/head/shot as a dose of monoclonal antibody) once a day for successive seven days, while the mice were weighed every day. As a control, a physiological saline was administered to five mice (an average body weight of 23 g/head) at a dose of 0.5 ml/head once a day for successive seven days, while the mice were weighed every day. Comparing the body weights of the mice administered with the above solution with those of the control mice, no difference was found between them. Also there was found no apparent abnormality in the mice administered with the above solution and in the control mice.

Industrial Applicability

As explained above, the monoclonal antibody of the present invention specifically reacts with IFNα8 and its mutant proteins. Thus, the monoclonal antibody has various uses in detecting and purifying such IFNα8 and its mutant proteins. The monoclonal antibody with such usefulness can be easily obtained in a desired amount by a production method using a hybridoma. The present invention with such outstanding effects and functions is a distinctly significant invention that greatly contributes to this art.

The invention claimed is:

1. An isolated monoclonal anti-human interferon (IFN) α antibody, said monoclonal antibody being produced from either hybridoma mAb-IFNα8#139 (accession no. FERM BP-11081) or hybridoma mAb-IFNα8Y36-2 (accession no. FERM BP-11082).

2. The monoclonal antibody of claim 1, which has an activity of neutralizing the anti-viral activity of human IFNα8.

3. A hybridoma, which produces the monoclonal antibody of claim 1 and is selected from the group consisting of hybridoma mAb-IFNα8#139 (accession no. FERM BP-11081) and hybridoma mAb-IFNα8Y36-2 (accession no. FERM BP-11082).

4. A pharmaceutical composition or a clinical diagnostic agent, which comprises the monoclonal antibody of claim 1.

* * * * *